(12) United States Patent
Suzuki et al.

(10) Patent No.: US 8,193,350 B2
(45) Date of Patent: Jun. 5, 2012

(54) FLUORESCENT COMPOUND AND LABELING AGENT COMPRISING THE SAME

(75) Inventors: Koji Suzuki, Yokohama (JP); Keitaro Umezawa, Yokohama (JP); Hiroshi Makino, Yokohama (JP); Daniel Citterio, Yokohama (JP)

(73) Assignee: Keio University, Tokyo (JP)

( * ) Notice: Subject to any disclaimer, the term of this patent is extended or adjusted under 35 U.S.C. 154(b) by 532 days.

(21) Appl. No.: 12/226,725

(22) PCT Filed: Apr. 27, 2007

(86) PCT No.: PCT/JP2007/059168
§ 371 (c)(1),
(2), (4) Date: Mar. 11, 2009

(87) PCT Pub. No.: WO2007/126052
PCT Pub. Date: Nov. 8, 2007

(65) Prior Publication Data
US 2009/0176313 A1 Jul. 9, 2009

(30) Foreign Application Priority Data
Apr. 28, 2006 (JP) ................................ 2006-126208

(51) Int. Cl.
*C07F 5/02* (2006.01)
(52) U.S. Cl. ........................ 544/181; 544/229
(58) Field of Classification Search .................. None
See application file for complete search history.

(56) References Cited

U.S. PATENT DOCUMENTS

| | | | |
|---|---|---|---|
| 5,248,782 A | 9/1993 | Haugland et al. | |
| 5,433,896 A | 7/1995 | Kang et al. | |
| 6,005,113 A | 12/1999 | Wu et al. | |

FOREIGN PATENT DOCUMENTS

| | | |
|---|---|---|
| JP | 2002-134275 A | 5/2002 |
| JP | 2002-169275 A | 6/2002 |
| WO | WO 2007/044866 A2 | 4/2007 |

OTHER PUBLICATIONS

Ballou et al., "Fluorescence imaging of tumors in vivo," Curr. Med. Chem, 2005, vol. 12, No. 7, pp. 795-805 (Abstract only).
Burgess et al., "New Chemistry of BODIPY Dyes, and BODIPY Dye Cassettes Featuring Through-Bond Energy Transfer," Advances in Nucleic Acid and Protein Analyses, Manipulation and Sequencing, Proceedings of SPIE, vol. 3926 (2000), pp. 95-105.
Burghart et al., "3,5-Diaryl-4,4-difluoro-4-bora-3a,4a-diaza-s-indacene (BODIPY) Dyes: Synthesis, Spectroscopic, Electrochemical, and Structural Properties," J. Org. Chem, 1999, vol. 64, No. 21, pp. 7813-7819 (Abstract only).
Chen et al., "4,4-Difluoro-4-bora-3a,4a-diaza-s-indacene (BODIPY) Dyes Modified for Extended Conjugation and Restricted Bond Rotations," J. Org. Chem. 2000, vol. 65, pp. 2900-2906.
Extended European Search Report issued Apr. 28, 2011, in European Patent Application No. 07742603.9.
Zhao et al., "Conformationally Restricted Aza-BODIPY: Highly Fluorescent, Stable Near-Infrared Absorbing Dyes," Chem. Eur. J. 2006, vol. 12, pp. 7254-7263.

*Primary Examiner* — Yong Chu
*Assistant Examiner* — Michael Barker
(74) *Attorney, Agent, or Firm* — Birch, Stewart, Kolasch & Birch, LLP

(57) ABSTRACT

A novel fluorescent compound having a high light fastness, high fluorescence quantum yield and sharp absorption spectrum, which emits fluorescence having a wavelength in long wavelength region, as well as its use as a labeling agent, is disclosed. In Formula [I] below, by forming a specific hetero ring(s) with $R^1$ and $R^2$, and/or $R^6$ and $R^7$, shift of the wavelength of the fluorescence to longer wavelength and increase in molar extinction coefficient are attained maintaining the high light fastness, high fluorescence quantum yield and sharp absorption spectrum which the fluorescent dyes having the boron dipyrromethene skeleton have.

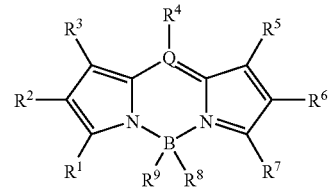

[I]

14 Claims, 1 Drawing Sheet

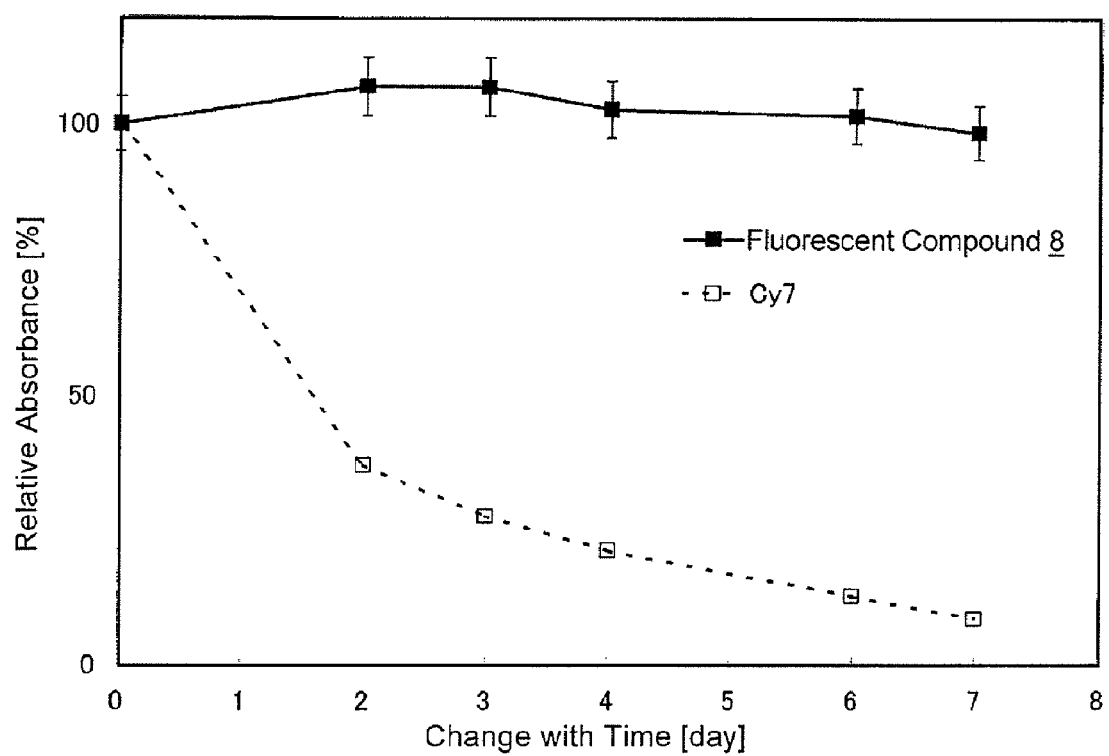

FLUORESCENT COMPOUND AND LABELING AGENT COMPRISING THE SAME

TECHNICAL FIELD

The present invention relates to a fluorescent compound and a labeling agent composed of the same.

BACKGROUND ART

Fluorescent dyes are used for the purpose of visualizing a sample, and are widely used in the biological and biochemical fields as a labeling material (labeling dye), orthochromatic dye, recognition probe of biologically relevant substances, and for photodynamic therapy (PDT). Fluorescent dyes having absorbance and fluorescence in the long wavelength region, especially in near infrared region (particularly, 650 nm to 900 nm) can be measured even in the presence of biological substances such as body tissues, blood, lipids and water without being optically disturbed by these substances. Further, in view of the advantages such as low energy and high optical permeation, application thereof to the imaging of tissues at a deep part in the body is expected.

Fluorescent dyes having a long wavelength are used not only in the biological and biochemical fields, but also in chemical and other fields. For example, they are often used widely as a red display material or laser dye, or as an optical recording material. Thus, fluorescent dyes with a long wavelength are demanded not only in biological field but also in a wide variety of fields.

The properties demanded for an excellent fluorescent dye with a long wavelength, e.g., for a fluorescent dye for labeling biological substances include the following:
1) fluorescence with a long wavelength;
2) high molar extinction coefficient;
3) high fluorescence quantum yield;
4) sharp absorption spectrum;
5) unresponsiveness to environment (response to solvent is small); and
6) variety of wavelengths (dyes with various wavelengths can be synthesized).

At present, as a molecule satisfying a part of the above-mentioned conditions, boron dipyrromethene skeleton (4,4-difluoro-4-bora-3a,4a-diaza-s-indacenes) represented by the following structural formula is known:

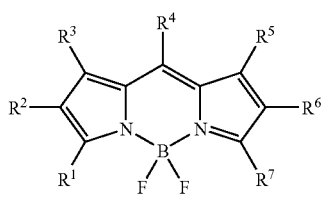

Although boron dipyrromethene skeleton is an excellent dye having a high light fastness, high fluorescence quantum yield and sharp absorption spectrum, it does not have a sufficient function as a near infrared fluorescent dye because the fluorescence wavelength of the basic skeleton is about 500 nm. Thus, some researches have been conducted for making the wavelength of boron dipyrromethene longer. The methods therefor include 1) introduction of a strong electron donating group(s); 2) making the skeleton stiffer; and 3) extension of conjugated system.

As for 1), as represented by, for example, Patent Literature 1 or Non-patent Literature 1, the shift of the wavelength to the longer wavelength can be attained by introducing strong electron donating groups as $R^1$ and $R^7$. However, increase in the molar extinction coefficient has not been attained thereby. Further, since the stronger the electron donating properties of the introduced functional groups, the more likely the photoinduced electron transfer (PET) occurs, so that the decrease in the fluorescence quantum yield occurs and the dependence of the fluorescence quantum yield on the polarity of the solvent becomes stronger. More particularly, since the fluorescence quantum yield of these molecules are drastically decreased in a polar solvent such as water or methanol, they are not suited for biological analyses.

As for 2), as represented by, for example, Non-patent Literature 2, it has been reported that shift of wavelength to longer wavelength is attained by crosslinking the electron donating groups introduced as $R^1$ and $R^7$ with $R^2$ and $R^6$, respectively, through an appropriate methylene chain or a hetero atom. However, increase in the molar extinction coefficient has not been attained thereby, and the synthetic method is complicated so that variation of the compounds is limited.

The above-mentioned 3) is a method wherein the shift of wavelength to longer wavelength is attained by extending the conjugated double bond such as olefin as in cyanine dyes. However, as frequently reported for cyanine dyes, there is a concern that decrease in the photostability and fluorescence quantum yield due to photoisomerization of the olefin may occur, so that it is not an effective method. Further, although shift of the wavelength to longer wavelength can be attained by fusing aromatic rings with $R^2$ and $R^3$, and $R^5$ and $R^6$, respectively, increase in the molar extinction coefficient has not been attained thereby. Further, by the reported synthetic method, the ring which can be fused is limited to an aromatic ring, so that the variation of the dye is limited.

Patent Literature 1: U.S. Pat. No. 5,248,782 B
Patent Literature 2: U.S. Pat. No. 5,433,896 B
Patent Literature 3: U.S. Pat. No. 6,005,113 B
Non-patent Literature 1: A. Burghart et. al. J. Org. Chem. 1999, 64, 7813.
Non-patent Literature 2: J. Chen et. al. J. Org. Chem. 2000, 65, 2900.
Non-patent Literature 3: Current Medicinal Chemistry 2005, 12, 795-895.

DISCLOSURE OF THE INVENTION

Problems to be Solved by the Invention

Accordingly, an object of the present invention is to provide a novel fluorescent compound having a high light fastness, high fluorescence quantum yield and sharp absorption spectrum, which emits a fluorescence with a wavelength in long wavelength region and which has a high molar extinction coefficient, as well as use thereof as a labeling agent.

Means for Solving the Problems

As a result of intensive study, the present inventors discovered that by forming a specific hetero ring(s) with $R^1$ and $R^2$, and/or $R^6$ and $R^7$ in the above-described boron dipyrromethene skeleton, shift of the wavelength of the fluorescence to longer wavelength and increase in molar extinction coefficient are attained maintaining the high light fastness, high fluorescence quantum yield and sharp absorption spectrum which the fluorescent dyes having the boron dipyrromethene skeleton have, thereby completing the present invention.

That is, the present invention provides a fluorescent compound having the structure represented by the following Formula [I]:

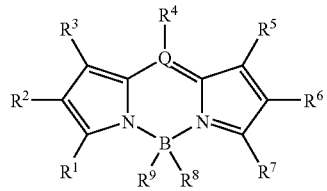

[I]

(wherein
R$^1$ and R$^2$ together form a 5-membered or 6-membered hetero ring containing at least one hetero atom selected from the group consisting of sulfur, oxygen, nitrogen and phosphorus, or when they do not form the hetero ring, R$^1$ and R$^2$ independently represent a hydrogen atom or an optional group which does not inhibit the fluorescence of the compound;

R$^6$ and R$^7$ together form a 5-membered or 6-membered hetero ring containing at least one hetero atom selected from the group consisting of sulfur, oxygen, nitrogen and phosphorus, or when they do not form the hetero ring, R$^6$ and R$^7$ independently represent a hydrogen atom or an optional group which does not inhibit the fluorescence of the compound;

at least one of (1) R$^1$ and R$^2$, and (2) R$^6$ and R$^7$ form the hetero ring;

Q represents a carbon atom or nitrogen atom;

R$^3$, R$^4$ and R$^5$ independently represent a hydrogen atom or an optional group which does not inhibit the fluorescence of the compound (provided that when Q is a nitrogen atom, R$^4$ does not exist); and R$^8$ and R$^9$ independently represent a halogen atom, alkyl group, alkenyl group, alkynyl group, alkoxy group, aryl group or heteroaryl group).

The present invention also provides a labeling agent composed of the compound according to the present invention. The present invention further provides a method for measuring a labeled substance, the method comprising subjecting a substance labeled with the labeling agent of the present invention to a reaction; and, after the reaction, measuring the substance with making the labeling agent emit light.

Effect of the Invention

By the present invention, a novel fluorescent compound having a high light fastness, high fluorescence quantum yield and sharp absorption spectrum, which emits a fluorescence with a wavelength in long wavelength region and which has a high molar extinction coefficient was provided. Since the fluorescent compound according to the present invention has a long fluorescence wavelength, measurement can be attained even in the presence of biological substances such as body tissues, blood, lipids and water without being optically disturbed by these substances. Further, because of the advantages such as low energy and high optical permeation, application thereof to the imaging of tissues at a deep part in the body can be attained. Still further, it may be used as a red display material or laser dye and an optical recording material, and for photodynamic therapy (PDT). Since the fluorescent compound of the present invention has a high fluorescence quantum yield and a high molar extinction coefficient, measurement with high sensitivity can be attained by using the compound as a labeling agent.

BRIEF DESCRIPTION OF THE DRAWINGS

FIG. 1 A figure showing the change with time of the absorbance of each of the Fluorescent Compound 8 of the present invention and a commercially available fluorescent compound Cy7 (trade name).

BEST MODE FOR CARRYING OUT THE INVENTION

As described above, the fluorescent compound of the present invention has the chemical structure represented the above-described Formula [I]. In Formula [I], R$^1$ and R$^2$ together form a 5-membered or 6-membered hetero ring containing at least one hetero atom selected from the group consisting of sulfur, oxygen, nitrogen and phosphorus, or when they do not form the hetero ring, R$^1$ and R$^2$ independently represent a hydrogen atom or an optional group which does not inhibit the fluorescence of the compound. Similarly, R$^6$ and R$^7$ together form a 5-membered or 6-membered hetero ring containing at least one hetero atom selected from the group consisting of sulfur, oxygen, nitrogen and phosphorus, or when they do not form the hetero ring, R$^6$ and R$^7$ independently represent a hydrogen atom or an optional group which does not inhibit the fluorescence of the compound. At least one of (1) R$^1$ and R$^2$, and (2) R$^6$ and R$^7$ form the hetero ring. By the hetero ring(s), shift of the fluorescence to longer wavelength is attained.

As the above-described hetero ring, those represented by any of the following formulae are preferred. In cases where two above-described hetero rings are formed, the two hetero rings are independent to each other.

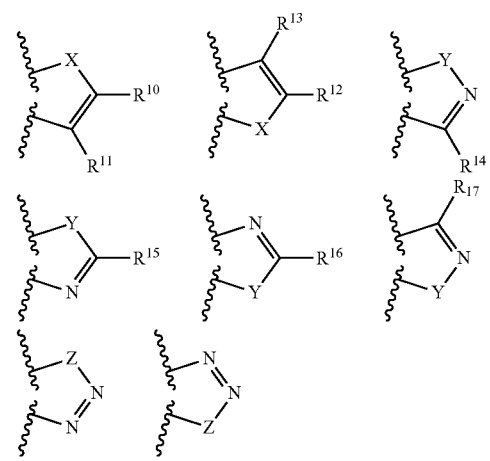

In these formulae, X, Y and Z independently represent sulfur, oxygen, nitrogen or phosphorus atom; R$^{10}$ to R$^{17}$ independently represent a hydrogen atom or an optional group which does not inhibit the fluorescence of said compound. In each of these formulae, the two wavy lines at the left side schematically indicate a moiety of the compound of the present invention to which the hetero ring is bound. As is apparent from the above-described formulae showing the preferred hetero rings, most preferred hetero rings are 5-membered. Further, those containing an oxygen atom or sulfur atom as the hetero atom are preferred. Among the hetero rings represented by the above-described formulae, those having the chemical structure represented by any of the following formulae are especially preferred.

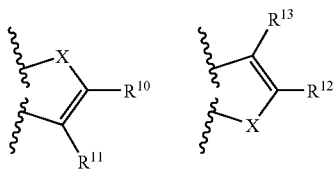

In these formulae, $R^{10}$ to $R^{17}$ independently represent a hydrogen atom or an optional group which does not inhibit the fluorescence of the fluorescent compound of the present invention (the optional group which does not inhibit the fluorescence of the fluorescent compound of the present invention will be described jointly in the section explaining $R^3$ to $R^5$). As $R^{10}$ to $R^{17}$, groups having electron donating property are preferred because the wavelength of the fluorescence is made longer. Especially, the higher the electron donating property, the more preferred because the wavelength of the fluorescence is shifted more to longer wavelength. In cases where two of $R^{10}$ to $R^{17}$ exist in one hetero ring, at least one of them is preferably a group having electron donating property.

Examples of the electron donating group include alkyl groups, phenyl group, p-alkoxyphenyl groups, p-dialkylaminophenyl groups, 2-thienyl group, 2-furyl group and dialkoxyphenyl groups (preferably 3,6-dialkoxyphenyl groups). In these groups, the number of carbon atoms in the alkyl group or in the alkyl moiety of the group having alkyl group is not restricted and is preferably 1 to about 10. Among these electron donating groups, $C_1$-$C_{10}$ alkyl groups and alkoxyphenyl group whose alkyl moiety has 1 to 10 carbon atoms are preferred.

In the above-described Formula [I], Q represents a carbon atom or nitrogen atom. In cases where Q is a nitrogen atom, the wavelength of the fluorescence is shifted more to longer wavelength than in cases where Q is a carbon atom. However, even in cases where Q is a carbon atom, by introducing an electron-withdrawing group (for example, nitro group, cyano group, trifluoromethyl group or the like) as $R^4$, the wavelength of the fluorescence is shifted to longer wavelength to a degree comparable in cases where Q is a nitrogen atom.

$R^3$, $R^4$ and $R^5$ independently represent a hydrogen atom or an optional group which does not inhibit the fluorescence of the compound of the present invention. When Q is a nitrogen atom, $R^4$ does not exist.

Examples of the optional groups which do not inhibit the fluorescence of the compound of the present invention, represented by $R^3$ to $R^5$; $R^1$ and $R^2$, or $R^6$ and $R^7$ when they do not form the hetero ring; and $R^{10}$ to $R^{17}$ in the preferred hetero rings described above, include those listed below. The term "does not inhibit fluorescence" herein means that the group does not shorten the wavelength of the fluorescence, does not decrease molar extinction coefficient, and does not decrease the fluorescence quantum yield, at all or substantially (preferably, each of the above-mentioned amounts of the compound having the group is not less than 95% of the same compound except that it does not have the group). In cases where the group which does not inhibit fluorescence has a site recognized by the target ion or target compound described below, although the fluorescence varies depending on whether the group is bound to the target, the term "does not inhibit fluorescence" means that the fluorescence is not inhibited in at least any one of the cases where the group is bound with the target and where the group is not bound with the target.

halogen atoms, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups.

In these substituent groups, "alkyl group" preferably has 1 to 20 carbon atoms, and may be any of linear, branched and circular (that is, cycloalkyl group). In this case, none of the hydrogen atoms contained in the alkyl group may be substituted, or one or more of them may be substituted with at least one selected from the group consisting of halogen atoms, nitro group, cyano group, hydroxyl group, amino group, thiol group, carboxyl group, aldehyde group, sulfonic group, isocyanate group, thioisocyanate group, aryl groups and heteroaryl groups. The above explanation is also applied to the alkyl groups in the groups containing an alkyl moiety, such as alkoxyl group and alkylthio group. The above-described substituent group(s) on the alkyl group is(are) not necessary.

In the above-described substituent groups, "alkenyl group" preferably has 2 to 20 carbon atoms, and may be any of linear, branched and circular (that is, cycloalkenyl group). In this case, none of the hydrogen atoms contained in the alkenyl group may be substituted, or one or more of them may be substituted with at least one selected from the group consisting of halogen atoms, nitro group, cyano group, hydroxyl group, amino group, thiol group, carboxyl group, aldehyde group, sulfonic group, isocyanate group, thioisocyanate group, aryl group and heteroaryl group. However, these substituent groups on the alkenyl group are not necessary.

In the above-described substituent groups, "alkynyl group" preferably has 2 to 20 carbon atoms, and may be any of linear, branched and circular (that is, cycloalkynyl group). In this case, none of the hydrogen atoms contained in the alkynyl group may be substituted, or one or more of them may be substituted with at least one selected from the group consisting of halogen atoms, nitro group, cyano group, hydroxyl group, amino group, thiol group, carboxyl group, aldehyde group, sulfonic group, isocyanate group, thioisocyanate group, aryl groups and heteroaryl groups. However, these substituent groups on the alkynyl group are not necessary.

In each of the above-described substituent groups (including those substituting on the above-described alkyl group, alkenyl group and alkynyl group), as the aryl group, aromatic rings and fused polycyclic aromatic rings having 1 to 4 aromatic rings are preferred, and preferred examples include phenyl group, 1- and 2-naphthyl groups, 1-, 2- and 9-anthranyl groups and 1-, 2- and 4-pyrenyl groups. In these cases, none of the hydrogen atoms contained in the aromatic rings may be substituted, or one or more of them may be substituted with at least one selected from the group consisting of halogen atoms, nitro group, cyano group, hydroxyl group, amino group, thiol group, carboxyl group, aldehyde group, sulfonic group, isocyanate group, thioisocyanate group, aryl groups, heteroaryl groups, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups and halogenosulfonyl groups. However, these substituent groups on the aryl group are not necessary.

In each of the above-described substituent groups (including those substituting on the above-described alkyl group, alkenyl group and alkynyl group), as the heteroaryl group, aromatic rings (5- or 6-membered rings) having 1 to 3 hetero atoms, and those wherein one or two aromatic rings are fused to the hetero aromatic ring are preferred. As the hetero atoms, oxygen, nitrogen and sulfur are preferred, and the combination thereof is not restricted. Preferred examples thereof include 2- and 3-furyl groups, 2- and 3-thienyl groups, N-, 2- and 3-pyrrolyl groups, 2- and 3-benzofuranyl groups, 2- and 3-benzothienyl groups, N-, 2- and 3-indolyl groups, N-, 1- and 2-isoindolyl groups, 2-, 3- and 4-pyridyl groups, 2-, 3- and 4-quinolyl groups, 1-, 3- and 4-isoquinolyl groups, 2-, 4- and 5-(1,3-oxazolyl) groups, 2-benzoxazolyl group, 2-, 4- and 5-(1,3-thiazolyl) groups, 2-benzothiazolyl group, N-, 2- and 4-imidazolyl groups, N- and 2-benzimidazolyl groups, 1- and 2-naphthofuranyl groups, 1- and 2-naphthothienyl groups, N-, 2- and 3-benzindolyl groups and the like. In this case, none of the hydrogen atoms contained in the hetero aromatic rings may be substituted, or one or more of them may be substituted with at least one selected from the group consisting of halogen atom, nitro group, cyano group, hydroxyl group, amino group, thiol group, carboxyl group, aldehyde group, sulfonic group, isocyanate group, thioisocyanate group, aryl group, heteroaryl group, alkyl group, alkenyl group, alkynyl group, alkoxy group, alkoxycarbonyl group, acyl group, halogenoacyl group, monoalkylamino group, dialkylamino group, alkylthio group, alkylcarbonylamide group, alkylamide carbonyl group, monoalkylsilyl group, dialkylsilyl group, trialkylsilyl group, monoalkoxysilyl groups, dialkoxysilyl group, trialkoxysilyl groups, alkylsulfonyl group and halogenosulfonyl group. However, these substituent groups on the heteroaryl group are not necessary.

In the above-described Formula [I], $R^8$ and $R^9$ each independently represents a halogen atom, alkyl group, alkenyl group, alkynyl group, alkoxy group, aryl group or heteroaryl group. Here, as for the alkyl group, alkenyl group, alkynyl group, alkoxy group, aryl group and heteroaryl group, the above-described explanation for $R^3$-$R^5$ and $R^{10}$-$R^{17}$ is applied as it is. $R^8$ and $R^9$ are preferably each independently a halogen atom, and both of them are especially preferably fluorine atoms.

The fluorescent compound of the present invention may have one or more of the following functional groups (1) to (6) as the optional group(s) which does(do) not inhibit the fluorescence of the fluorescent compound of the present invention. In cases where the optional group which does not inhibit the fluorescence is an aryl group or heteroaryl group, the aryl group or heteroaryl group may be substituted with one or more of the following functional groups.

(1) Binding Group

The fluorescent compound of the present invention preferably has at least one binding group. The term "binding group" herein means a group which can be used for binding the compound of the present invention to another compound. Since a fluorescent labeling agent is often bound to a biologically relevant substance such as a protein, polypeptide or sugar, preferred examples include amino group, hydroxyl group, carboxyl group, sulfonic group, thiol group, disulfide group, isocyanate group, thioisocyanate group, succinimidyl ester group, pentafluorophenyl ester group, maleimide group and the like, which are convenient to the binding with the biologically relevant substances. Since it is sufficient that these groups can be used for the binding with another compound, an optional group (for example, aminoalkyl group or the like) having at least any one of these groups may also be used as the binding group. Although it is sufficient if only one binding group exists, and it is usually preferred that only one binding group exist in order to restrict the binding site to one site, the compound may have 2 or more binding groups. Further, amino group, hydroxyl group, carboxyl group, sulfonic group or the like may be bound to a part of the voluminous group described below, thereby the group may also simultaneously be used as both the binding group and as the voluminous group.

(2) Voluminous Group

To increase the yield of synthesis, the fluorescent compound of the present invention preferably has at least one voluminous group. Since boron dipyrromethene skeleton moiety in the fluorescent compound of the present invention is highly planar, the entire compound is also often planar. In such a case, planar molecules are stacked and π-bonds are formed between the aromatic rings of different molecules, so that the molecules are bound through the π-π bonds (π-π stacking) to form aggregations, thereby the yield may be decreased. To avoid such a situation and to assure that the synthesis yield be not decreased, the compound preferably has at least one voluminous group which prevents the π-π stacking as $R^1$ to $R^{17}$ in Formula [I], or as a substituent to be introduced to an aryl group or heteroaryl group. The "voluminous group" herein means a group having a larger thickness in the direction of thickness (the direction perpendicular to the plane defined by the boron dipyrromethene skeleton) than at least a linear alkyl group, and preferred examples are branched alkyl groups and branched alkoxyl groups having not less than 10 carbon atoms, preferably 10 to 20 carbon atoms.

(3) Lipid Solubility- or Water Solubility-Adjusting Group

Further, as required, the compound may have at least one group adjusting the solubility (lipid solubility or water solubility). Since a fluorescent labeling agent is often used in aqueous system, in cases where it is desired to increase the hydrophilicity of the fluorescent compound so as to increase the solubility in aqueous system, the compound may have at least one hydrophilic group. Examples of such a hydrophilic group include, but not limited to, alkyl groups and alkoxyl groups (carbon number is preferably 1 to 6) having one or more of hydroxyl group, amino group, carbonyl group, carboxyl group, sulfonic group, ether bonds and the like. Such a hydrophilic group may also simultaneously be used as the above-described voluminous group and/or binding group. In cases where it is desired to increase lipid solubility, an alkyl group(s) each having not less than 10 carbon atoms, preferably 10 to 20 carbon atoms, or an aryl group(s), or a group(s) having both of these groups may be incorporated in the compound. The fluorescent compounds 2 to 5 according to the present invention synthesized in the Examples below have the group having the following chemical structure as $R^4$ as a group increasing lipid solubility.

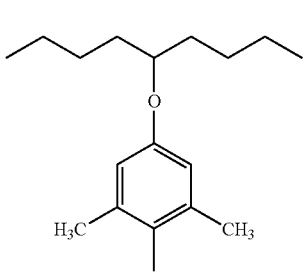

In this group, the ether moiety is contained in order to make the synthesis easier. The two methyl groups on the benzene ring inhibit the rotational rotary motion of this substituent group so as to prevent decrease in fluorescence quantum yield due to the rotary motion of this substituent group.

(4) Chemiluminescence Group

Chemiluminescence group is a group having a structure which emits light as a result of a chemical reaction. By introducing a chemiluminescent group(s) to the fluorescent compound of the present invention, the fluorescent dye moiety emits fluorescence by the light emitted by the chemiluminescent group, and this fluorescence is measured. Therefore, the chemiluminescence group is not necessarily one which emits a visible light, but may be anyone as long as it emits a light which can excite the fluorescent dye moiety to make it emit fluorescence. As such a chemiluminescent group, any of those used as a labeling agent in this field may be employed and various groups are known or well-known. Preferred examples thereof include phthalcarbazide derivatives, dioxetane derivatives, lophine derivatives, acridine derivatives, indole derivatives, oxalic acid derivatives, diphenoyl derivatives and luciferin derivatives, and all of these are well-known in this field. These chemiluminescent groups are represented by the following formulae, respectively.

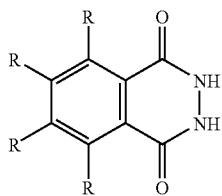

Phthalhydrazide Derivatives

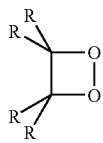

Dioxetane Derivatives

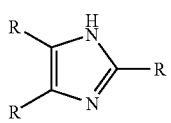

Lophine Derivatives

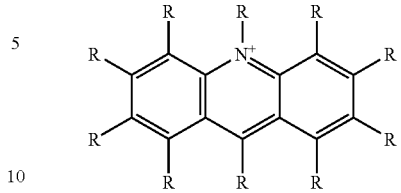

Acridine Derivatives

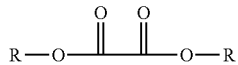

Dioxetane Derivatives

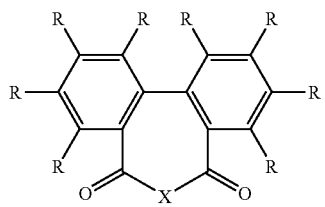

Diphenoyl Derivatives
(X: —O—, —O—O—)

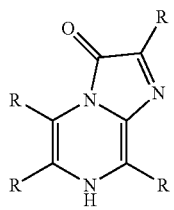

Luciferin Derivatives (5) Polymerization Site to Polymer (Molecule Having Unsaturated Double Bond at its Terminal)

The fluorescent compound of the present invention preferably has at least one polymerization site. The term "polymerization site" herein means a site to be copolymerized with an organic macromolecule. It is known that fluorescent intensity or molar extinction coefficient is increased and so the detection sensitivity is increased by introducing a dye to an organic macromolecule. Further, by copolymerizing the dye, the dye does not leak (elute) to the solvent, so that it is suited for continuous measurement using an organic macromolecule film. As the polymerization site, any of those having a vinyl group may be employed. Specific examples thereof include, but not limited to, vinylalkyl groups, vinylalkoxy groups, vinylalkoxycarbonyl groups, vinyl aryl groups, vinyl heteroaryl groups and the like.

(6) Recognition Site by Target Ion or Target Compound (Group which Selectively Captures a Specific Ion or Substance, Such as a Crown Ether)

By introducing a group such as benzocrown, azacrown or N-arylazacrown, which recognizes an ion or molecule, or by introducing a group such as p-dimethylaminophenyl group which responds to the polarity of ambient solvent (pH or polarity of solvent), it is possible to make the compound have a function as a fluorescent probe which recognizes a specific substance or environment and convert the recognition to optical information. In this case, since the electron donating property of the recognition site changes before and after the recognition of the target, the optical properties of the dye also change accordingly. In the most preferred mode, the recognition site is introduced to the above-described $R^4$, $R^{10}$, $R^{12}$, $R^{15}$ or $R^{16}$, but the site where the recognition site is introduced is not restricted thereto. The term "recognition site" herein means the site which captures the target ion or target compound. In general, in cases where the fluorescent compound has a recognition site and where a specific substance is to be measured, it is preferred that the optical response change before and after the recognition. For example, the specific substance can be measured utilizing the change in the fluorescence quantum yield or the shift of the wavelength of the maximum absorption or fluorescence.

The fluorescent compound of the present invention can be produced, for example, as follows: That is, an azide compound is synthesized by adding ethyl azide acetate to a heteroaryl ring having a formyl group at an optional position, and the synthesized azide compound is heated to reflux in toluene to fuse pyrrole to the heteroaryl ring. After deprotecting the carboxylic acid ethyl ester at the α-position of the pyrrole, the resultant is heated in the presence of a strong base to decarbonate the carboxylic acid at the α-position. This pyrrole ring is fused with an aromatic ring having a formyl group to synthesize a dipyrromethene compound. The method for synthesizing a dipyrromethene compound is not restricted to this method, and a dipyrromethene compound can also be obtained by, for example, allowing reaction between pyrrole rings in the presence of a trialkyl orthoformate and an acid catalyst; or by carrying out a reaction with a hetero pyrrole ring having a formyl group in the presence of an acid. Alternatively, a dipyrroazamethene compound having a nitrogen atom in the crosslinking part can be synthesized by nitrosating the heteropyrrole ring with sodium nitrite. The desired compound is obtained by reacting the obtained dipyrromethene compound or dipyrroazamethene compound in the presence of triethylamine and trifluoroboron diethyl ether complex. When the heteroaryl ring has an halogen atom or boronic acid, an optional aryl ring or heteroaryl ring can be directly bound by Suzuki coupling, so that dyes having a variety of wavelength can be provided.

That is, the fluorescent compound of the present invention can be synthesized by, for example, first synthesizing a fused ring between the hetero ring formed with $R^1$ and $R^2$, and/or with $R^6$ and $R^7$, and a pyrrole ring as described above; binding two fused rings via one carbon atom by the reaction with dichloromethane; and binding the $BR^8R^9$ moiety by reacting $BF_3$ or the like. In cases where the compound has a substituent group(s), the obtained product can be further bound with the substituent group(s). In cases where $R^4$ is a substituent group, by reacting a compound having the substituent group simultaneously with the above-mentioned dichloromethane, the substituent group can be bound to the carbon atom of the dichloromethane simultaneously with the binding of the fused rings through dichloromethane. Since a plurality of synthesis methods are described in detail in the Examples below, the fluorescent compounds of the present invention can be easily produced by those skilled in the art referring thereto.

The fluorescent compound of the present invention can be used as a fluorescent labeling agent. Fluorescent labeling agents per se are well-known, and the fluorescent compound of the present invention can also be used in the same manner as the conventional fluorescent labeling agents. That is, the fluorescent compound of the present invention is bound to a substance to be labeled, thereby labeling the substance. In cases where the fluorescent compound of the present invention has the above-described binding group, the fluorescent compound of the present invention is bound with the substance to be labeled through the binding group by a conventional method. In cases where the fluorescent compound does not have a binding group, an intermediate having a binding group is prepared by a conventional method, and the intermediate can be bound to the substance to be labeled.

The mode of using the fluorescent labeling agent may be exactly the same as that of the conventional fluorescent labeling agents. That is, after labeling the substance to be labeled as described above, the labeled substance (in the present Description, this is referred to as "labeled substance") is subjected to a reaction, and after a washing step(s) and the like as required, an excitation light is radiated to the label to emit fluorescence, and the fluorescence is measured. The "reaction" herein may be an antigen-antibody reaction in case of immunoassay, and hybridization between nucleic acids in case of detection of a nucleic acid, and the like, but the "reaction" is not restricted thereto. For example, in case of an immunoassay wherein fluorescent labeling agents are widely used, the labeling agent can be used as follows: For example, in cases where a target antigen in a test sample is to be measured by a sandwich immunoassay, a primary antibody to the target antigen is immobilized on a solid phase, the immobilized primary antibody is then reacted with the test sample, thereby binding the target antigen in the test sample to the immobilized primary antibody. After washing, a secondary antibody labeled with the fluorescent labeling agent is then reacted. After washing, the fluorescent labeling agent attached to the secondary antibody bound with the target antigen is made to emit fluorescence with an excitation light by a conventional method, and the fluorescence is measured. The optimum wavelength of the excitation light can be easily determined by measuring the absorption maximum wavelength of each fluorescent compound. The optimum wavelength of the excitation light is usually about 570 nm to 680 nm, preferably about 660 nm to 680 nm. In the present Description and Claims, the term "measure" includes any of detection, quantification and semi-quantification.

Further, fluorescent labeling agents are widely used not only in the above-described sandwich method, but also in other immunoassays such as immunohistochemistry. Still further, detection of a nucleic acid having a specific base sequence is widely carried out with labeling the nucleic acid with a fluorescent labeling agent, and the fluorescent labeling agent of the present invention can be applied to these uses similarly to the conventional fluorescent labeling agents.

Still further, the fluorescent compound of the present invention can be used as a red fluorescent dye in various fields including red display materials, laser dyes and optical recording materials.

The fluorescent compound of the present invention has a peak fluorescence wavelength in the region of long wavelength region of orange to near infrared at a wavelength of about 580 nm to 700 nm. When the fluorescent compound is used as a labeling agent, it can be measured even in the presence of biological substances such as body tissues, blood, lipids and water without being optically disturbed by these substances. Further, in view of the advantages such as low energy and high optical permeation, it can be applied to the imaging of tissues at a deep part in the body. For example, by labeling a polyclonal antibody, monoclonal antibody, singlestranded antibody, peptide chain, sugar chain or the like which specifically accumulates in a particular organ or tumor cells in an animal, and injecting the labeled substance to the animal, the labeling agent accumulates in the particular organ or the tumor cells. Thus, by imaging the animal with a CCD camera or the like, the particular organ or the tumor cells can be visualized. However, examples of the in vivo imaging are not restricted to this. Further, the compound can be used as a red display material or laser dye, an optical recording material, and for photodynamic therapy (PDT). Still further, since the fluorescent compound of the present invention has a high fluorescence quantum yield and a high molar extinction coefficient, measurement with a high sensitivity can be attained by using the compound as a labeling agent.

The present invention will now be described more concretely by way of Examples. However, the present invention is not restricted to the following Examples.

Example 1

Synthesis of Fluorescent Compound 1 of the Present Invention

In accordance with the reaction scheme below, a fluorescent compound 1 of the present invention was synthesized. In the reaction scheme (and also in the reaction schemes described below), "r.t." means room temperature.

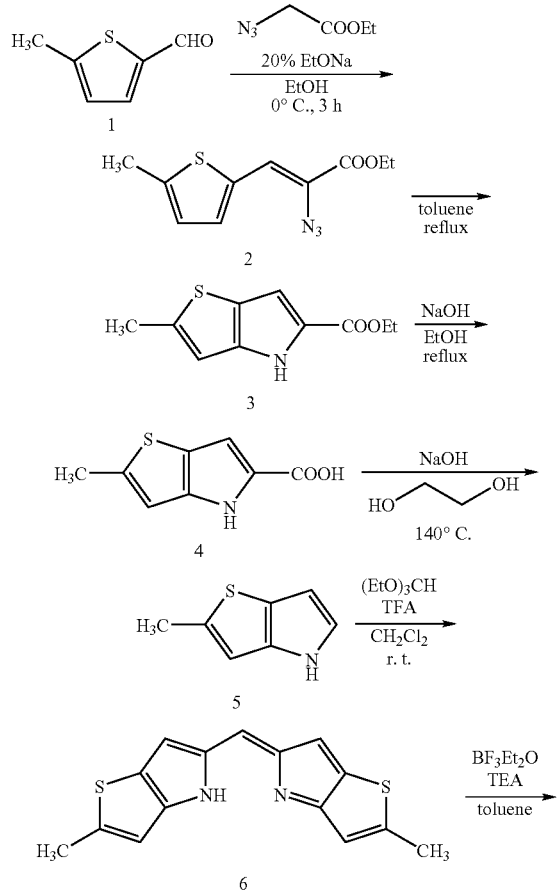

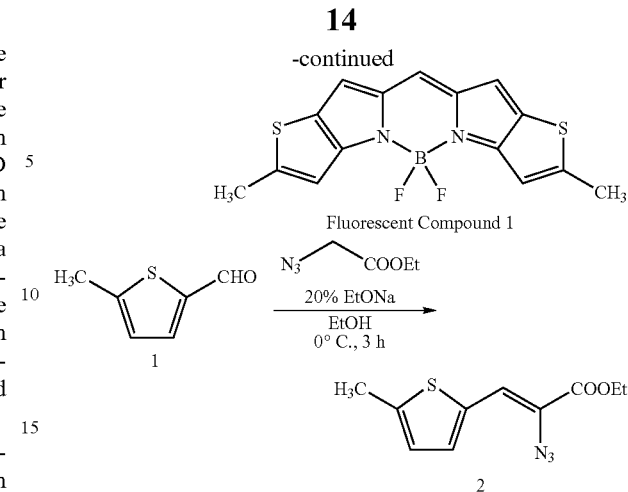

Under Ar gas flow, to a solution (100 mL) of 5-methyl-2-thiophencarbaldehyde 1 (3.67 g, 29.1 mmol, 1.0 eq.) and ethyl azide acetate (7.51 g, 58.2 mmol, 2.0 eq.) in ethanol, a solution obtained by diluting 20% solution of sodium ethoxide (19.9 g, 58.3 mmol, 2.0 eq.) in ethanol with ethanol (50 mL) was slowly added dropwise at 0° C. After stirring the mixture for 3 hours, saturated aqueous ammonium chloride solution was added to change the pH to neutral, and generated yellow precipitates were separated by filtration, followed by washing the precipitates with water and drying the precipitates under vacuum. The obtained crude product was purified by column chromatography (silica gel, hexane:ethyl acetate=9:1) to obtain pale yellow liquid 2 (3.61 g).

TLC (silica): $R_f$=0.8 (silica gel, hexane:ethyl acetate=4:1)

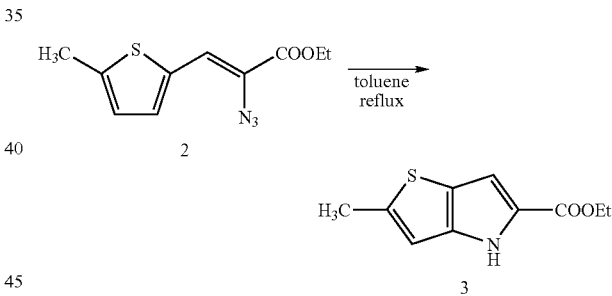

A solution of 2 in toluene (60 mL) was stirred for 30 minutes under reflux. After concentration under reduced pressure, the obtained crude product was purified by column chromatography (silica, hexane:ethyl acetate=9:1) to obtain pale flesh solids 3 (1.82 g, 25.0%).

TLC (silica): Rf=0.3 (hexane:ethyl acetate=4:1)

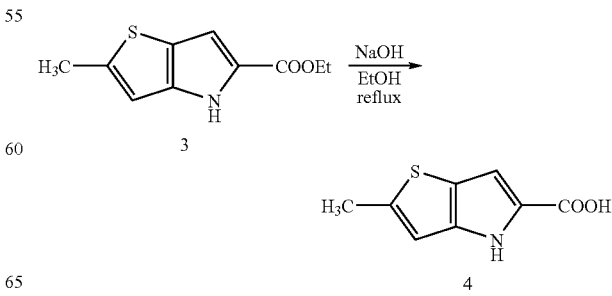

To a solution (100 mL) of 3 (1.82 g, 8.70 mmol, 1 eq.) in ethanol, an aqueous solution (50 mL) of sodium hydroxide (5.35 g, 134 mmol, 15.4 eq.) was added, and the mixture was stirred for 30 minutes under reflux. After allowing the mixture to cool, 6N aqueous hydrochloric acid solution was added. After separating the generated precipitates by filtration, the precipitates were washed with water and dried under vacuum to obtain white solids 4 (1.41 g, 89.5%).

TLC (silica): Rf=0.2 (hexane:ethyl acetate=1:1)

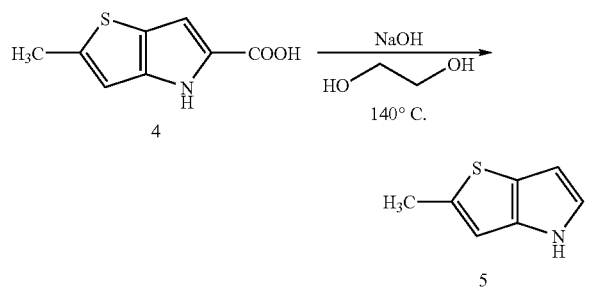

To a solution (20 mL) of 4 (571 mg, 3.15 mmol, 1 eq.) in ethylene glycol, sodium hydroxide (1.34 g, 33.5 mmol, 10.6 eq.) was added, and the mixture was stirred at 140° C. for 4 hours under Ar gas flow. After allowing the mixture to cool, ethyl acetate was added and the resulting mixture was washed twice with water and once with saturated brine. After drying the resulting mixture over anhydrous sodium sulfate, the mixture was concentrated under reduced pressure and the obtained brown oily crude product was purified by column chromatography (silica, hexane:ethyl acetate=4:1) to obtain brown liquid 5 (303 mg, 70.1%).

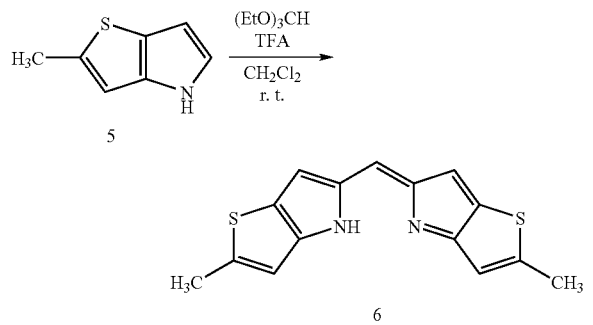

To a solution (5 mL) of 5 (56.8 mg, 0.414 mmol, 2 eq.) in methylene chloride, triethyl orthoformate (1.00 mL, 6.21 mmol, 30 eq.) was added, and the mixture was stirred at room temperature under Ar gas flow. One drop of trifluoroacetic acid was added, and the resulting mixture was stirred for another 90 minutes at room temperature. The reaction was stopped by adding a large amount of water, and the organic layer was washed once with saturated aqueous sodium hydrogen carbonate solution, once with water and once with saturated brine. After drying the resulting mixture over anhydrous sodium sulfate, the mixture was concentrated under reduced pressure, and the obtained crude product was purified by column chromatography (alumina, chloroform:ethyl acetate=3:1) to obtain violet solids 6 (57.5 mg).

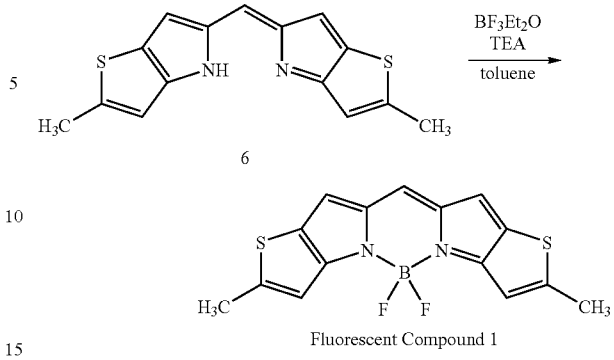

Fluorescent Compound 1

In toluene (10 mL), 6 (57.5 mg, 0.201 mmol, 1 eq.) was dissolved, and triethylamine (0.3 ml, 2.08 mmol, 10 eq.) and trifluoroboron diethyl ether complex (0.40 mL, 3.11 mmol, 15 eq.) were added, and the mixture was heated to reflux for 1 hour. After allowing the resulting mixture to cool, the insoluble product was separated by silica gel chromatography and the eluted solution was concentrated under reduced pressure. The obtained crude product was purified by column chromatography (silica, toluene) to obtain the fluorescent compound 1 in the form of green lustrous solids (5.8 mg, 8.46%, 2 steps).

TLC (silica) $R_f$=0.6 (toluene)

$^1$H-NMR (300 MHz, CDCl$_3$) σ2.59 (s, 6H), 6.89 (s, 2H), 6.95 (s, 2H), 7.24 (s, 1H)

Example 2

Synthesis of Fluorescent Compound 2

In accordance with the reaction scheme below, a fluorescent compound 2 of the present invention was synthesized. In the reaction scheme (and also in the reaction schemes described below), "DDQ" means 2,3-dicyano-5,6-dichloro-p-benzoquinone (a type of oxidizing agent).

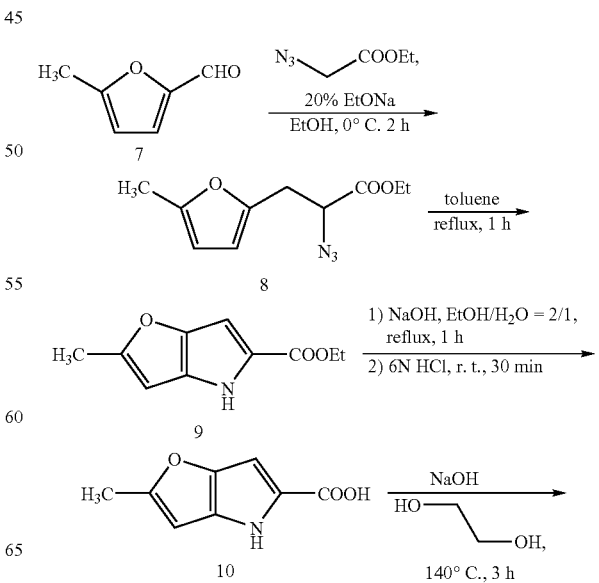

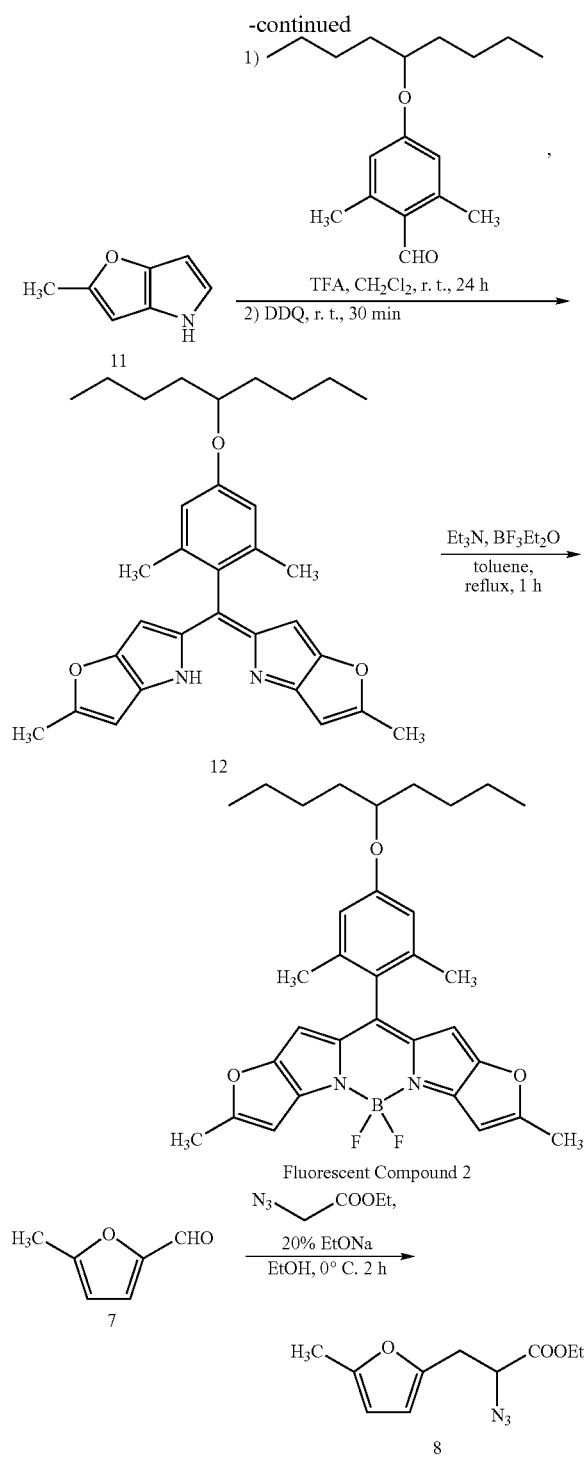

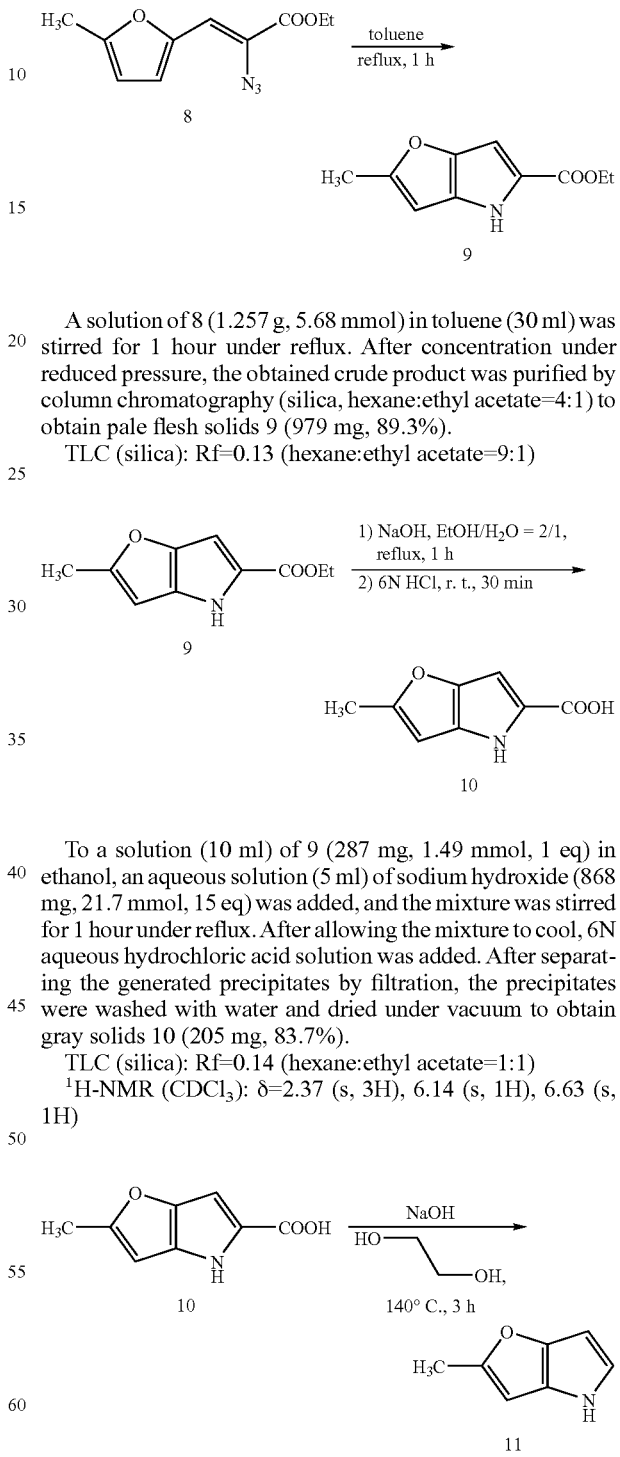

centrated under reduced pressure and the obtained crude product was purified by column chromatography (silica gel, hexane:ethyl acetate=9:1) to obtain pale yellow liquid 8 (1.26 g, 34.8%).

TLC (silica): $R_f$=0.42 (silica gel, hexane ethyl acetate=9:1)

A solution of 8 (1.257 g, 5.68 mmol) in toluene (30 ml) was stirred for 1 hour under reflux. After concentration under reduced pressure, the obtained crude product was purified by column chromatography (silica, hexane:ethyl acetate=4:1) to obtain pale flesh solids 9 (979 mg, 89.3%).

TLC (silica): Rf=0.13 (hexane:ethyl acetate=9:1)

To a solution (10 ml) of 9 (287 mg, 1.49 mmol, 1 eq) in ethanol, an aqueous solution (5 ml) of sodium hydroxide (868 mg, 21.7 mmol, 15 eq) was added, and the mixture was stirred for 1 hour under reflux. After allowing the mixture to cool, 6N aqueous hydrochloric acid solution was added. After separating the generated precipitates by filtration, the precipitates were washed with water and dried under vacuum to obtain gray solids 10 (205 mg, 83.7%).

TLC (silica): Rf=0.14 (hexane:ethyl acetate=1:1)

$^1$H-NMR (CDCl$_3$): δ=2.37 (s, 3H), 6.14 (s, 1H), 6.63 (s, 1H)

Under Ar gas flow, to a solution (90 ml) of 5-methyl-2-furaldehyde 7 (1.80 g, 16.3 mmol, 1 eq) and ethyl azide acetate (2.80 g, 32.7 mmol, 2 eq) in ethanol, a solution obtained by diluting 20% solution of sodium ethoxide (11.1 ml, 32.7 mmol, 2 eq) in ethanol with ethanol (30 ml) was slowly added dropwise at 0° C. After stirring the mixture for 2 hours, saturated aqueous ammonium chloride solution was added to change the pH to neutral, and ethyl acetate was added. The resulting mixture was washed twice with water and once with saturated brine. After drying the resulting mixture over anhydrous sodium sulfate, the mixture was con- To a solution (5 ml) of 10 (200 mg, 1.21 mmol, 1 eq) in ethylene glycol, sodium hydroxide (484 mg, 12.1 mmol, 10 eq) was added, and the mixture was stirred at 140° C. for 3 hours under Ar gas flow. After allowing the mixture to cool, ethyl acetate was added and the resulting mixture was washed twice with water and once with saturated brine. After drying the resulting mixture over anhydrous sodium sulfate, the mixture was concentrated under reduced pressure and the obtained brown oily crude product was purified by column chromatography (silica, 9:1 hexane/ethyl acetate) to obtain brown liquid 11 (68.0 mg, 45.5%).

TLC (silica): $R_f$=0.62 (hexane:ethyl acetate=4:1)

$^1$H-NMR (CDCl$_3$): δ=2.39 (s, 3H), 6.07 (s, 1H), 6.12 (d, 1H, J=2.9 Hz), 6.67 (t, 1H, J=2.9 Hz), 7.65 (bs, 1H)

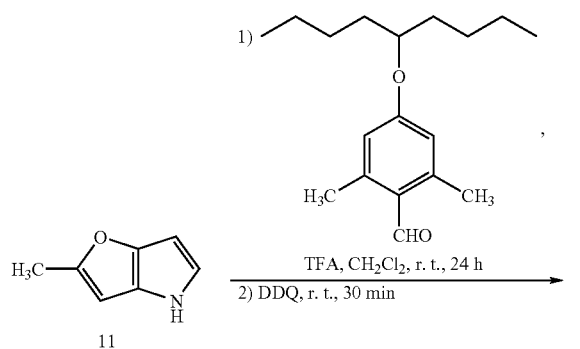

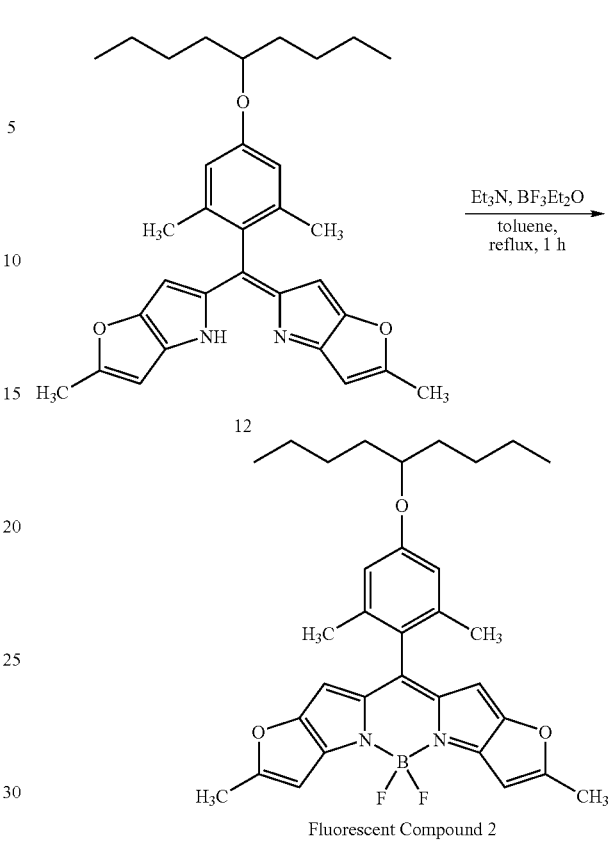

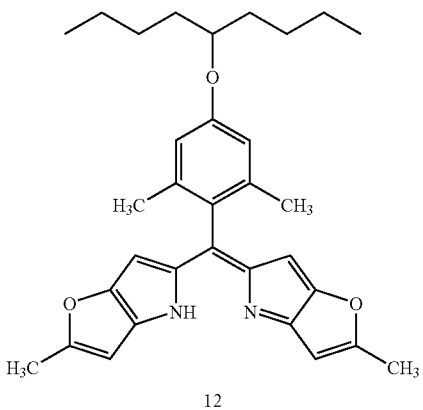

To a solution (25 ml) of 11 (60 mg, 0.5 mmol, 2 eq) in methylene chloride, 4-(1-butyl pentyloxy)-2,6-dimethylbenzaldehyde (69 mg, 0.25 mmol, 1 eq) was added. The mixture was deaerated under reduced pressure and the atmosphere was completely replaced with Ar. Three drops of trifluoroacetic acid were added, and after the mixture was stirred for 24 hours at room temperature, p-chloranil (62 mg, 0.25 mmol, 1 eq) was added. After the mixture was stirred for 1 hour at room temperature, the mixture was concentrated under reduced pressure and insoluble matters were separated by column chromatography (alumina, chloroform), followed by concentration of the filtrate to obtain violet solids 12. The obtained 12 was used in the next reaction without purification as it was.

The 12 wad added to toluene (10 ml), and triethylamine (0.2 ml) and trifluoroboron diethyl ether complex (0.3 ml) were added thereto. After the mixture was stirred for 1 hour at room temperature, the mixture was washed with saturated aqueous sodium hydrogen carbonate solution. The mixture was extracted three times with toluene and washed once with saturated brine. After drying the resulting mixture over anhydrous sodium sulfate, the mixture was concentrated under reduced pressure and the obtained crude product was purified by column chromatography (silica, hexane:ethyl acetate=4: 1) to obtain fluorescent compound 2 (22.0 mg, 18.2%, the overall yield from 11).

TLC (silica): $R_f$=0.50 (4:1 hexane/ethyl acetate)

$^1$H-NMR (CDCl$_3$): δ=0.85-0.96 (m, 6H), 1.22-1.29 (m, 8H), 1.42-1.68 (m, 4H), 2.15 (s, 6H), 2.44 (s, 6H), 4.25 (m, 1H), 5.97 (s, 2H), 6.34 (s, 2H), 6.63 (s, 2H)

Example 3

Synthesis of Fluorescent Compound 3

In accordance with the reaction scheme below, a fluorescent compound 3 of the present invention was synthesized.

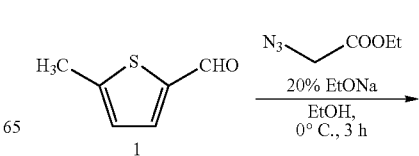

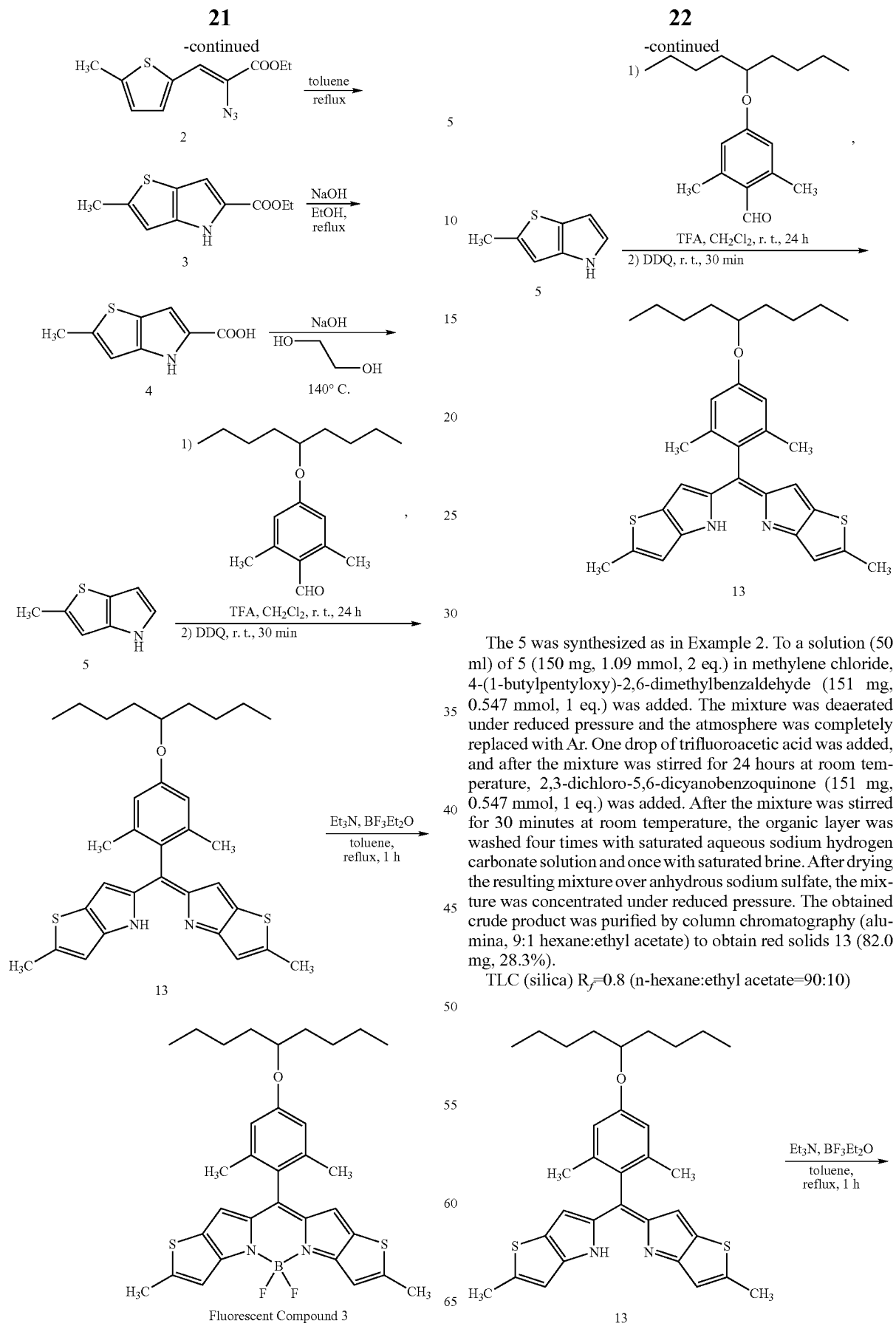

The 5 was synthesized as in Example 2. To a solution (50 ml) of 5 (150 mg, 1.09 mmol, 2 eq.) in methylene chloride, 4-(1-butylpentyloxy)-2,6-dimethylbenzaldehyde (151 mg, 0.547 mmol, 1 eq.) was added. The mixture was deaerated under reduced pressure and the atmosphere was completely replaced with Ar. One drop of trifluoroacetic acid was added, and after the mixture was stirred for 24 hours at room temperature, 2,3-dichloro-5,6-dicyanobenzoquinone (151 mg, 0.547 mmol, 1 eq.) was added. After the mixture was stirred for 30 minutes at room temperature, the organic layer was washed four times with saturated aqueous sodium hydrogen carbonate solution and once with saturated brine. After drying the resulting mixture over anhydrous sodium sulfate, the mixture was concentrated under reduced pressure. The obtained crude product was purified by column chromatography (alumina, 9:1 hexane:ethyl acetate) to obtain red solids 13 (82.0 mg, 28.3%).

TLC (silica) $R_f$=0.8 (n-hexane:ethyl acetate=90:10)

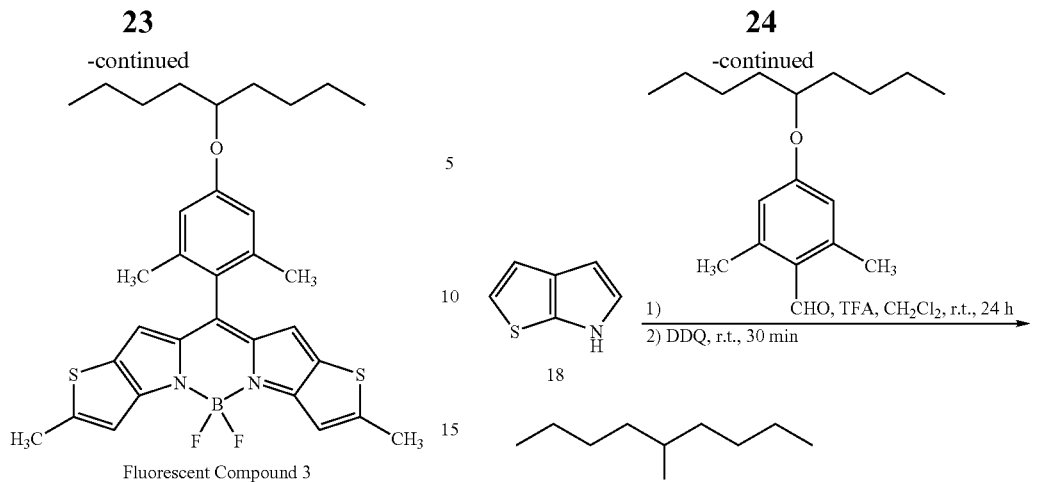

Fluorescent Compound 3

In toluene solution (10 ml), 13 (82.0 mg) was dissolved, and triethylamine (0.2 ml) and trifluoroboron ether complex (0.3 ml) were added. After the mixture was stirred for 1 hour at room temperature, the mixture was washed with saturated aqueous sodium hydrogen carbonate solution. The mixture was extracted three times with toluene and washed once with saturated brine. After drying the resulting mixture over anhydrous sodium sulfate, the mixture was concentrated under reduced pressure and the obtained crude product was purified by column chromatography (silica, hexane:ethyl acetate=4:1) to obtain Compound 3 (22.0 mg, 18.2%).

$^1$H-NMR (300 MHz, CDCl$_3$) σ0.94 (t, 6H, J=7.1 Hz), 1.35-1.45 (m, 8H), 1.65-1.72 (m, 4H), 2.15 (s, 6H), 2.58 (s, 6H), 4.25 (quant, 1H, J=5.9 Hz), 6.57 (s, 2H), 6.64 (s, 2H), 6.93 (s, 2H)

Example 4

Synthesis of Fluorescent Compound 4

In accordance with the reaction scheme below, a fluorescent compound 4 of the present invention was synthesized.

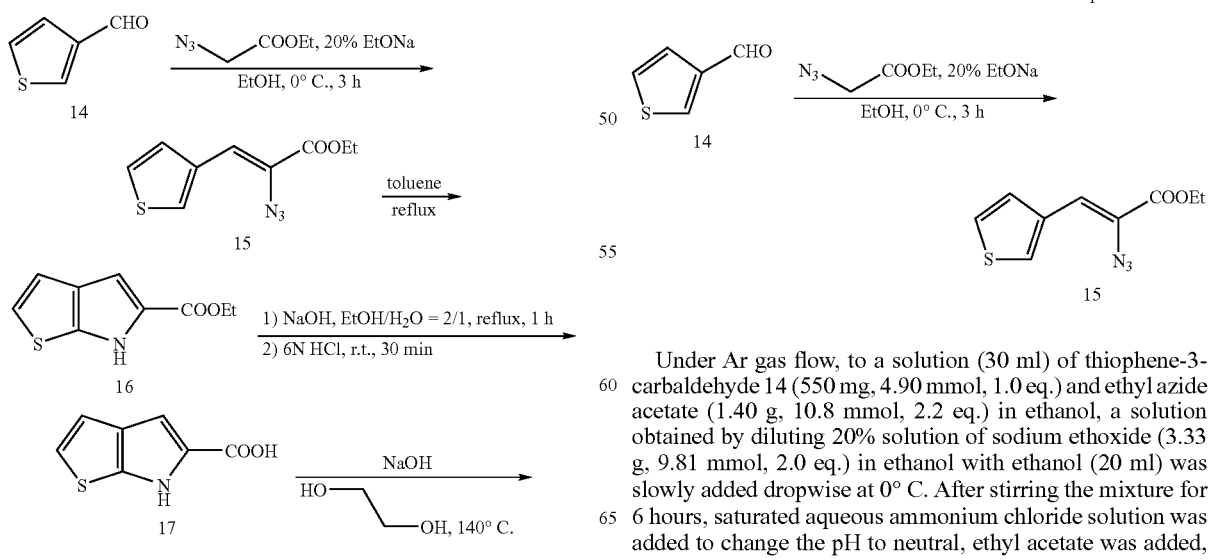

Fluorescent Compound 4

Under Ar gas flow, to a solution (30 ml) of thiophene-3-carbaldehyde 14 (550 mg, 4.90 mmol, 1.0 eq.) and ethyl azide acetate (1.40 g, 10.8 mmol, 2.2 eq.) in ethanol, a solution obtained by diluting 20% solution of sodium ethoxide (3.33 g, 9.81 mmol, 2.0 eq.) in ethanol with ethanol (20 ml) was slowly added dropwise at 0° C. After stirring the mixture for 6 hours, saturated aqueous ammonium chloride solution was added to change the pH to neutral, ethyl acetate was added, and the resulting mixture was washed twice with water and once with saturated brine. After drying the resulting mixture over anhydrous sodium sulfate, the mixture was concentrated under reduced pressure to obtain pale yellow liquid 15. The obtained 15 was used in the next reaction without purification.

TLC (silica): R$_f$=0.8 (silica gel, hexane:ethyl acetate=4:1)

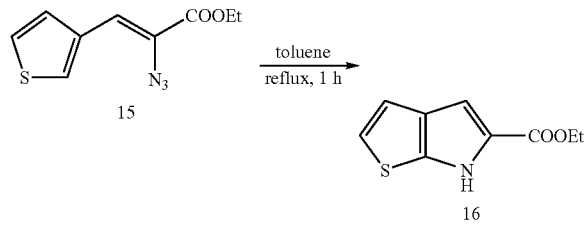

A solution of 15 in toluene (20 ml) was stirred for 30 minutes under reflux. After concentration under reduced pressure, the obtained crude product was purified by column chromatography (silica, hexane:ethyl acetate=3:1) to obtain pale flesh solids 16 (295 mg, 30.8%).

TLC (silica): Rf=0.5 (hexane ethyl acetate=4:1)

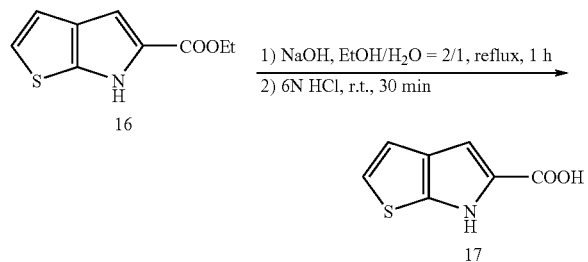

To a solution (10 ml) of 16 (226 mg, 1.16 mmol, 1 eq.) in ethanol, an aqueous solution (5 ml) of sodium hydroxide (740 mg, 18.5 mmol, 15.9 eq.) was added, and the mixture was stirred for 1 hour under reflux. After allowing the mixture to cool, 6N aqueous hydrochloric acid solution was added. Ethyl acetate was added to the reaction system and the resulting mixture was washed twice with water and once with saturated brine. After drying the resulting mixture over anhydrous sodium sulfate, the mixture was concentrated under reduced pressure to obtain gray solids 17 (190 mg, 97.7%).

TLC (silica): Rf=0.4 (hexane ethyl acetate=1:1)

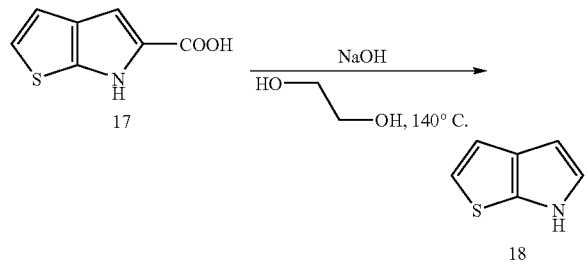

To a solution (5 mL) of 17 (190 mg, 1.14 mmol, 1 eq.) in ethylene glycol, sodium hydroxide (340 mg, 8.49 mmol, 7.4 eq.) was added, and the mixture was stirred for 2 hours at 140° C. under Ar gas flow. After allowing the mixture to cool, ethyl acetate was added and the resulting mixture was washed twice with water and once with saturated brine. After drying the resulting mixture over anhydrous sodium sulfate, the mixture was concentrated under reduced pressure and the obtained brown oily crude product was purified by column chromatography (silica, 9:1 hexane/ethyl acetate) to obtain brown liquid 18 (99.3 mg, 70.9%).

TLC (silica): Rf=0.62 (hexane:ethyl acetate=4:1)

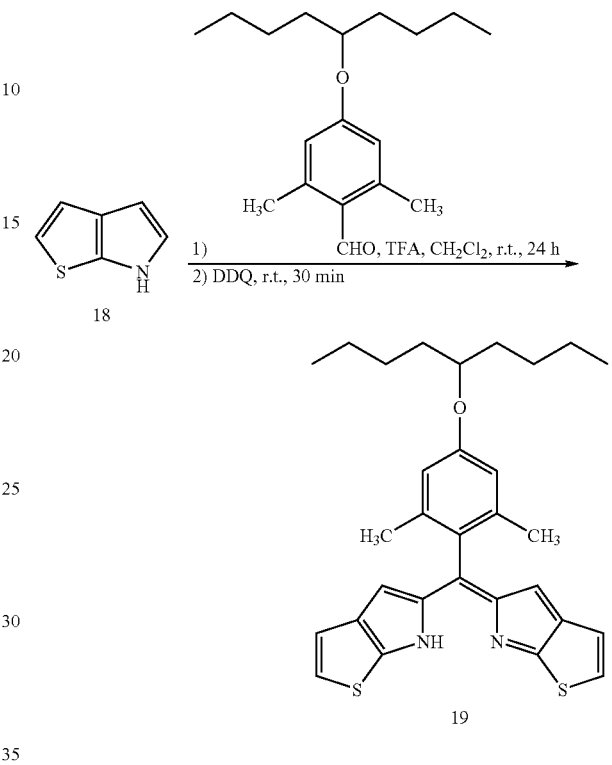

To a solution (50 mL) of 18 (93.0 mg, 0.755 mmol, 2 eq.) in methylene chloride, 4-(1-butylpentyloxy)-2,6-dimethylbenzaldehyde (102 mg, 0.377 mmol, 1 eq.) was added. The mixture was deaerated under reduced pressure and the atmosphere was completely replaced with Ar. One drop of trifluoroacetic acid was added, and after the mixture was stirred for 24 hours at room temperature, p-chloranil (120 mg, 0.488 mmol, 1.3 eq.) was added. After the mixture was stirred for 30 minutes at room temperature, the organic layer was washed four times with saturated aqueous sodium hydrogen carbonate solution and once with saturated brine. After drying the resulting mixture over anhydrous sodium sulfate, the mixture was concentrated under reduced pressure. The obtained crude product was purified by column chromatography (alumina, chloroform) to obtain red solids 19 (68.4 mg, 36.0%).

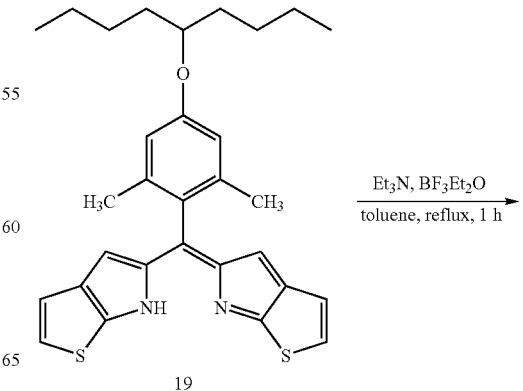

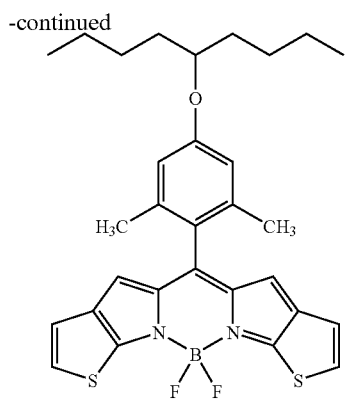

Fluorescent Compound 4

In toluene solution (5 ml), 19 (38.4 mg, 0.0764 mmol, 1 eq.) was dissolved, and triethylamine (0.20 mL, 1.38 mmol, 18 eq.) and trifluoroboron diethyl ether complex (0.30 mL, 2.30 mmol, 30 eq.) were added. After the mixture was stirred for 1 hour at room temperature, the mixture was washed with saturated aqueous sodium hydrogen carbonate solution. The mixture was extracted three times with toluene and washed once with saturated brine. After drying the resulting mixture over anhydrous sodium sulfate, the mixture was concentrated under reduced pressure. The obtained crude product was purified by column chromatography (silica, hexane:ethyl acetate=4:1) and gel permeation chromatography (chloroform) to obtain fluorescent compound 4 (7.4 mg, 17.7%).

TLC (silica) $R_f$=0.6 (toluene)

$^1$H-NMR (300 MHz, CDCl$_3$) σ0.94 (t, 6H, J=7.1 Hz), 1.34-1.44 (m, 8H), 1.65-1.72 (m, 4H), 2.16 (s, 6H), 2.58 (s, 6H), 4.27 (quant, 1H, J=5.9 Hz), 6.65 (s, 2H), 6.66 (s, 2H), 6.77 (d, 2H, J=5.3 Hz), 6.97 (d, 2H, J=5.3 Hz)

Example 5

Synthesis of Fluorescent Compound 5

In accordance with the reaction scheme below, a fluorescent compound 5 of the present invention was synthesized.

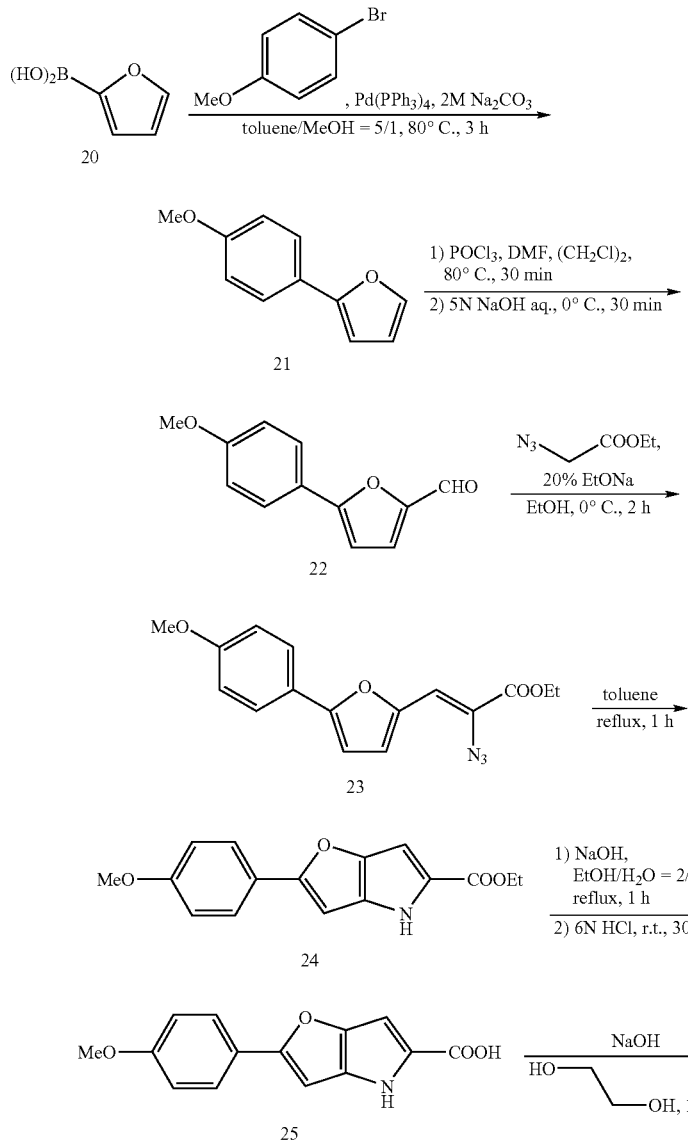

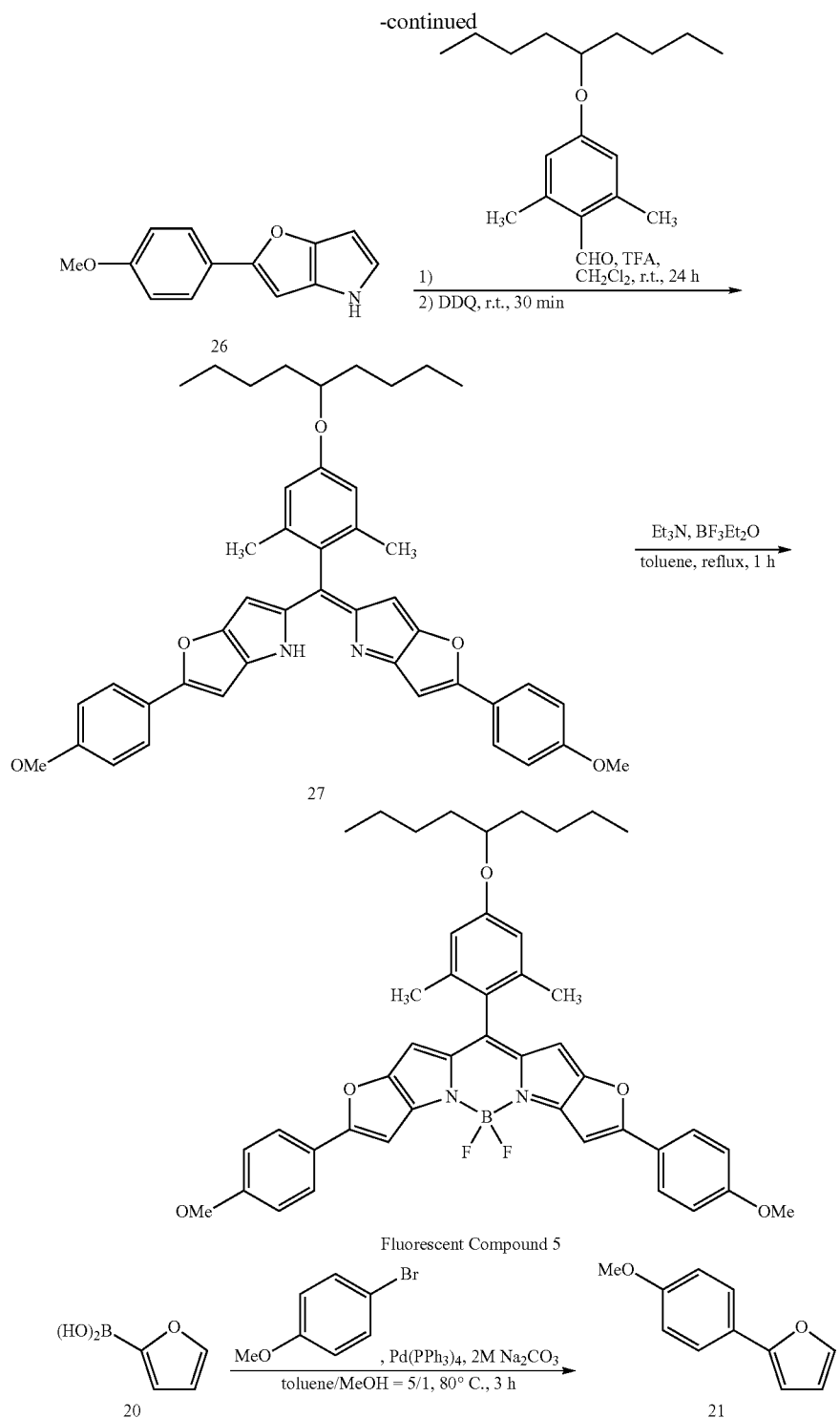

Fluorescent Compound 5

To a solution (320 mL) of 2-furan boronic acid 20 (6.00 g, 53.5 mmol, 1 eq) in 5:1 toluene/methanol, p-bromoanisole (10.0 g, 53.5 mmol, 1 eq) and 2M aqueous sodium carbonate solution (53 ml) were added. The mixture was deaerated under reduced pressure and the atmosphere was completely replaced with Ar. Tetrakis(triphenylphosphine)palladium(0) (619 mg, 0.535 mmol, 0.01 eq) was added, and the mixture was stirred for 3 hours at 80° C. After allowing the mixture to cool, the mixture was washed with saturated aqueous sodium hydrogen carbonate solution. The mixture was extracted three times with ethyl acetate and washed once with saturated brine. After drying the resulting mixture over anhydrous sodium sulfate, the mixture was concentrated under reduced pressure and the obtained crude product was purified by column chromatography (silica, 2:1 hexane:methylene chloride) to obtain orange solid 21 (4.42 g, 78.2%).

TLC (silica): $R_f$=0.66 (4:1 hexane/ethyl acetate)

¹H-NMR (CDCl₃): δ=3.84 (s, 3H), 6.45 (t, 1H, J=1.6 Hz), 6.51 (d, 1H, J=3.4 Hz), 6.92 (d, 2H, J=8.8 Hz), 7.43 (d, 1H, J=1.2 Hz), 7.60 (d, 1H, J=8.8 Hz)

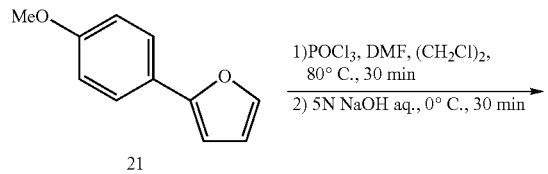

To a solution (20 ml) of 21 (700 mg, 4.0 mmol, 1 eq) in 1,2-dichloroethane, phosphoryl chloride (0.72 ml, 8.0 mmol, 2 eq) was added, and the mixture was stirred at room temperature for 5 minutes. N,N-dimethylformamide (0.62 ml, 8.0 mmol, 2 eq) was added and the mixture was stirred at 80° C. for 30 minutes. After allowing the mixture to cool, 5N aqueous sodium hydroxide solution was added dropwise at 0° C. Water was added and the resulting mixture was extracted 5 times with methylene chloride and washed once with saturated brine. After drying the resulting mixture over anhydrous sodium sulfate, the mixture was concentrated under reduced pressure and the obtained crude product was purified by column chromatography (silica, 4:1 hexane/ethyl acetate) to obtain orange fluid 22 (667.3 mg, 82.9%).

TLC (silica): R_f=0.40 (4:1 hexane/ethyl acetate) ¹H-NMR (CDCl₃): δ=3.87 (s, 3H), 6.72 (d, 1H, J=3.9 Hz), 6.97 (d, 2H, J=8.8 Hz), 7.31 (d, 1H, J=3.7 Hz), 7.77 (d, 2H, J=9.0 Hz), 9.60 (s, 1H)

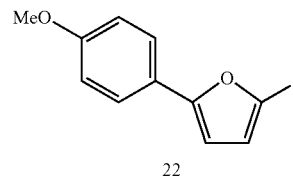

Under Ar gas flow, to a solution (10 ml) of 22 (202 mg, 1.0 mmol, 1 eq) and ethyl azide acetate (516 mg, 4.0 mmol, 4 eq) in ethanol, a solution obtained by diluting 20% solution of sodium ethoxide (1.4 ml, 4 mmol, 4 eq) in ethanol with ethanol (2 ml) was slowly added dropwise at 0° C. After stirring the mixture for 2 hours, saturated aqueous ammonium chloride solution was added to change the pH to neutral, ethyl acetate was added, and the resulting mixture was washed twice with water and once with saturated brine. After drying the resulting mixture over anhydrous sodium sulfate, the mixture was concentrated under reduced pressure and the obtained crude product was purified by column chromatography (silica, 9:1 hexane/ethyl acetate) to obtain orange solids 23 (273 mg, 87.5%).

TLC (silica): R_f=0.39 (9:1 hexane/ethyl acetate) ¹H-NMR (CDCl₃): δ=1.39 (t, 3H, J=7.1 Hz), 3.87 (s, 3H), 4.35 (q, 2H, J=7.1 Hz), 6.67 (d, 1H, J=3.7 Hz), 6.92 (s, 1H), 6.93 (d, 2H, J=7.6 Hz), 7.18 (d, 1H, J=3.4 Hz), 7.65 (d, 2H, J=8.3 Hz)

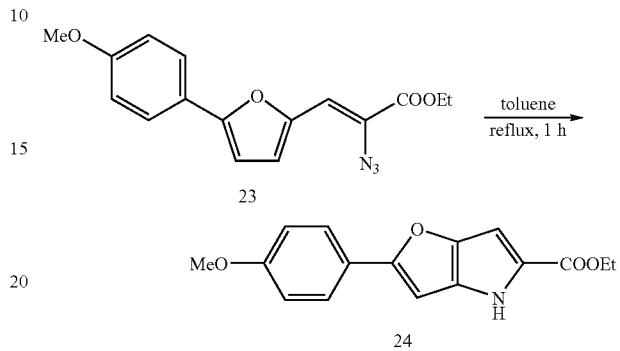

A solution (5 ml) of 23 (273 mg, 0.875 mmol) in toluene was stirred for 5 hours under reflux. After concentration under reduced pressure, the obtained crude product was purified by column chromatography (silica, chloroform) to obtain brown solids 24 (117 mg, 46.9%).

TLC (silica): R_f=0.35 (4:1 hexane/ethyl acetate) ¹H-NMR (CDCl₃): δ=1.38 (t, 3H, J=7.2 Hz), 3.84 (s, 3H), 4.35 (q, 2H, J=7.1 Hz), 6.57 (s, 1H), 6.80 (s, 1H), 6.94 (d, 2H, J=8.8 Hz), 7.66 (d, 2H, J=9.0 Hz), 8.78 (bs, 1H)

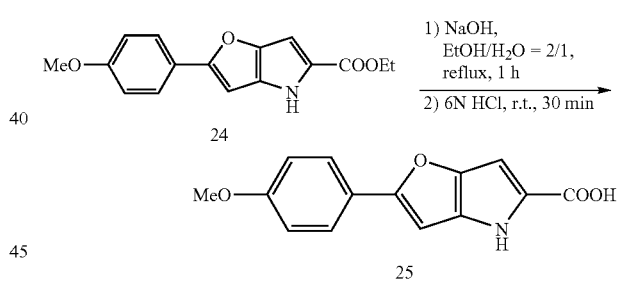

To a solution (10 ml) of 24 (71.0 mg, 0.25 mmol, 1 eq) in ethanol, an aqueous solution (5 ml) of sodium hydroxide (150 mg, 3.75 mmol, 15 eq) was added, and the mixture was stirred for 1 hour under reflux. After allowing the mixture to cool, 6N aqueous hydrochloric acid solution was added. Ethyl acetate was added and the mixture was washed twice with water and once with saturated brine. After drying the resulting mixture over anhydrous sodium sulfate, the mixture was concentrated under reduced pressure and dried under vacuum to obtain green solids 25 (60.0 mg, 93.0%).

TLC (silica): R_f=0.38 (ethyl acetate)

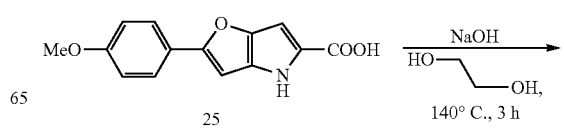

-continued

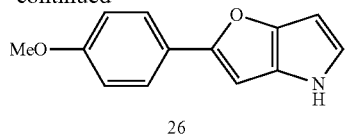
26

To a solution (4 ml) of 25 (140 mg, 0.55 mmol, 1 eq) in ethylene glycol, sodium hydroxide (200 mg, 5 mmol, 9 eq) wad added, and the mixture was stirred at 160° C. for 2 hours under Ar gas flow. After allowing the mixture to cool, ethyl acetate was added and the resulting mixture was washed twice with water and once with saturated brine. After drying the resulting mixture over anhydrous sodium sulfate, the mixture was concentrated under reduced pressure to obtain brown liquid 26 (138 mg). The obtained 26 was used in the next reaction without purification as it was.

TLC (silica): $R_f$=0.23 (4:1 hexane/ethyl acetate)

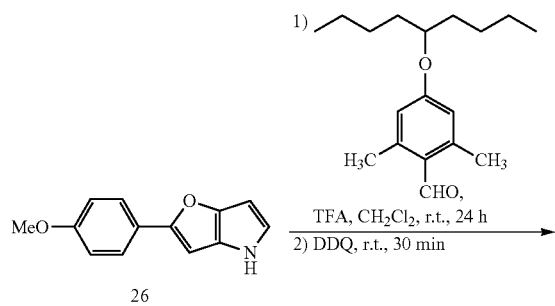

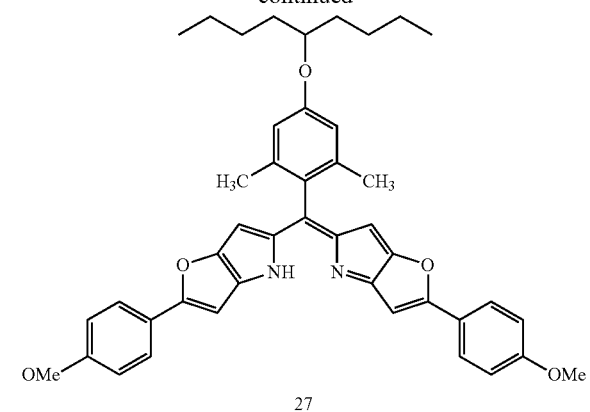
27

To a solution (30 ml) of 26 (67.0 mg, 0.31 mmol, 2 eq) in 1,2-dichloroethane, 4-(1-butylpentyloxy)-2,6-dimethylbenzaldehyde (42 mg, 0.15 mmol, 1 eq) was added. The mixture was deaerated under reduced pressure and the atmosphere was completely replaced with Ar. One drop of trifluoroacetic acid was added, and the resulting mixture was heated to reflux for 2 hours. After allowing the mixture to cool, the solvent was concentrated under reduced pressure to obtain bluish green solids 27. The obtained 27 was used in the next reaction without purification.

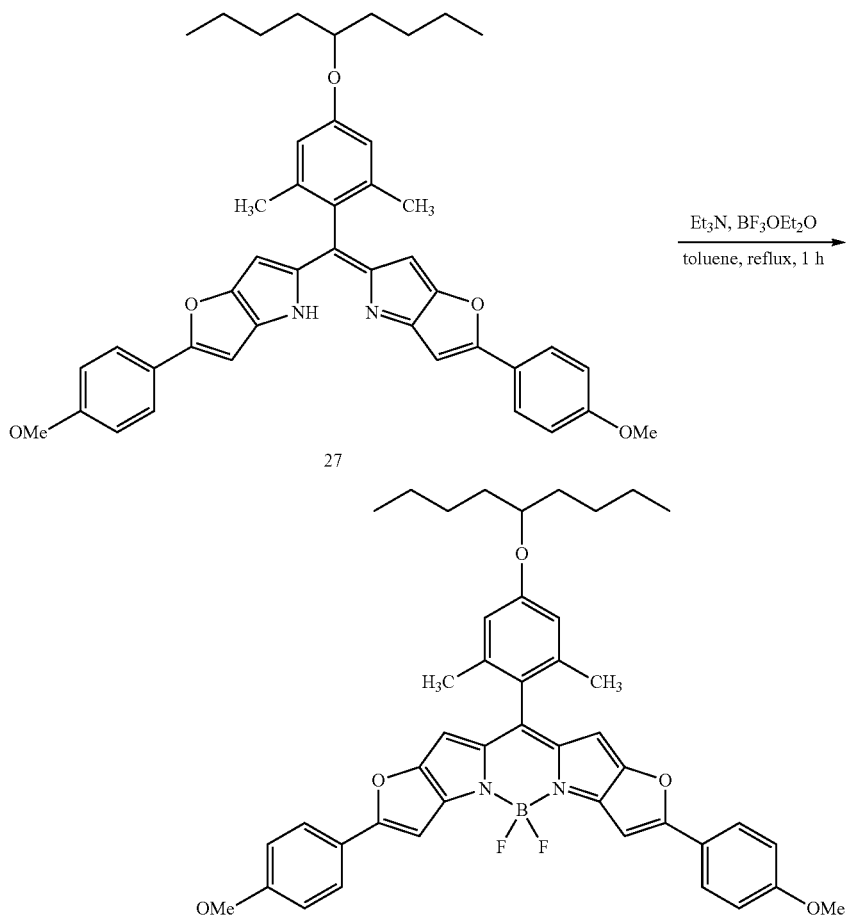

Fluorescent Compound 5

In toluene solution (5 ml), 27 was dissolved, and triethylamine (0.20 mL) and trifluoroboron diethyl ether complex (0.30 mL) were added. After the mixture was stirred for 30 minutes at room temperature, the mixture was washed with saturated aqueous sodium hydrogen carbonate solution. The mixture was extracted three times with chloroform and washed once with saturated brine. After drying the resulting mixture over anhydrous sodium sulfate, the mixture was concentrated under reduced pressure and the obtained crude product was purified by column chromatography (silica, chloroform) to obtain fluorescent compound 5 (0.9 mg, 0.5%, 2 steps).

TLC (silica): $R_f$=0.23 (1:1 toluene/chloroform) $^1$H-NMR (CDCl$_3$): δ=0.85-0.97 (m, 6H), 1.25-1.42 (m, 8H), 1.57-1.68 (m, 4H), 2.19 (s, 6H), 3.87 (s, 6H), 4.28 (m, 1H), 6.04 (s, 2H), 6.66 (s, 2H), 6.85 (s, 2H), 6.97 (d, 4H, J=9.0 Hz), 7.75 (d, 4H, J=9.0 Hz)

Example 6

Optical Properties

The absorption spectra and fluorescence emission spectra of the fluorescent compounds 2, 3 and 5 of the present invention synthesized in Examples 2, 3 and 5, respectively, were measured. Absorption spectra were measured using a commercially available spectrophotometer (U-2001, Hitachi), with measurement wavelengths of 300 nm to 750 nm at intervals of every 1 nm. The fluorescence emission spectra were measured using a commercially available fluorometer (F-4500, Hitachi) using an excitation light having the maximum absorption wavelength under the following conditions:

Measurement Wavelength: fluorescent compounds 2 and 3: 550 nm-700 nm
  fluorescent compound 5: 600 nm-750 nm
  perylene: 520 nm-700 nm
Measurement Wavelength Intervals: 0.2 nm
Scan Speed: 60 nm/min
Response: AUTO
Slit Width: Excitation Side 2.5 nm
  Light-receiving Side 2.5 nm
Photomultiplier: 700 V From the measured spectra, molar extinction coefficient ε (M$^{-1}$ cm$^{-1}$), fluorescence quantum yield Φ, and fwhm (full width at half maximum height) (nm) were calculated. The results are shown in Table 1 below.

TABLE 1

| Fluorescent Compound | Solvent | $\lambda_{abs}$ [nm] | $\lambda_{flu}$ [nm] | ε [M$^{-1}$cm$^{-1}$] | Φ | fwhm [nm] |
|---|---|---|---|---|---|---|
| 2 | CHCl$_3$ | 581 | 588 | 81,000 | 0.67 | 18 |
|   | THF | 577 | 584 | 80,000 | 0.64 | 18 |
|   | MeOH | 574 | 582 | 81,000 | 0.7 | 18 |
| 3 | CHCl$_3$ | 586 | 596 | 170,000 | 0.39 | 20 |
|   | THF | 582 | 592 | 170,000 | 0.31 | 20 |
|   | MeOH | 579 | 589 | 150,000 | 0.26 | 21 |
| 5 | CHCl$_3$ | 673 | 685 | 190,000 | 0.68 | 28 |
|   | THF | 669 | 680 | 190,000 | 0.67 | 27 |
|   | MeOH | 664 | 679 | 200,000 | 0.63 | 29 |

The fluorescence quantum yield Φ was calculated by using N,N'-bis(1-hexylheptyl)-3,4:9,10-perylenbis(dicarboxylmide) (Φ=1.00 in CH$_2$Cl$_2$) as a reference; substituting: A=A$_{ref}$=0.1, Φ$_{ref}$=1.00, n$_{ref}$=1.46 (CH$_2$Cl$_2$), n=1.484 (CHCl$_3$), 1.407 (THF), 1.3284 (MeOH); and substituting the integrated value of the area of fluorescence intensity detected by excitation with a wavelength of A=0.1, for F. The fluorescence quantum yield Φ is calculated according to the following equation:

$$\Phi=\Phi_{ref}\times(A_{ref}\times F\times n^2)/(A\times F_{ref}\times n_{ref}^2)$$

(wherein A represents absorbance, F represents integrated value of wave number of fluorescent spectrum; n represents the refractive index of the solvent; and "ref" represents the reference dye).

Optical Properties of Fluorescent Compounds 2 and 3

Fluorescent compounds 2 and 3 have maximum absorption wavelengths at 581 nm and 586 nm, respectively, so that the maximum absorption wavelength was shifted to longer wavelength by about 80 nm when compared with that of boron dipyrromethene (R$_1$=R$_3$=R$_5$=R$_7$=Me). Thus, the fluorescence wavelength of boron dipyrromethene was shifted to longer wavelength by the extension of π conjugation system brought about by the introduction of fused rings, as contemplated by the molecular design. Fluorescent compounds 2 and 3 emit intense and sharp fluorescence having maximum fluorescence wavelengths at 588 nm and 596 nm, respectively, and each fluorescence has a sharp spectrum. As seen from the values in Table 1, fwhm is as small as about 20 nm, which indicates that the spectrum is very sharp. These results indicate that the fluorescence wavelengths of the fluorescent compounds 2 and 3 are shifted to longer wavelength retaining the stiffness comparable to that of the boron dipyrromethene skeleton. Fluorescent compound 2 showed a high fluorescence quantum yield in both highly polar MeOH and lowly polar THF. This indicates that fluorescent compound 2 has a very low responsiveness to environment intrinsic to boron dipyrromethene. It is thought that fluorescent compound 2 emits a similar fluorescence in aqueous solvents having a higher polarity, so that it has the properties indispensable to the application of the compound to biological measurements.

Optical Properties of Fluorescent Compound 5

The maximum absorption wavelength of fluorescent compound 5 was 673 nm, so that the maximum absorption wavelength was shifted to longer wavelength by about 170 nm when compared with boron dipyrromethene (R$^1$=R$^3$=R$^5$=R$^7$=Me) and by about 90 nm when compared with fluorescent compound 2. As contemplated by the molecular design, it was successfully attained that the wavelength was shifted to longer wavelength when compared with boron dipyrromethene skeleton by the introduction of fused rings and by the introduction of electron donating groups and that the maximum absorption wavelength was shifted to the near infrared region. Fluorescent compound 5 emits intense and sharp fluorescence having the maximum fluorescence wavelength at 685 nm, and each fluorescence has a sharp spectrum. As seen from the values in Table 1, fwhm is as small as about 30 nm, which indicates that the spectrum is very sharp. These results indicate that fluorescent compound 5 has a stiffness of skeleton comparable to that of fluorescent compound 2 in spite of the fact that p-methoxyphenyl group was introduced. Fluorescent compound 5 showed a high fluorescence quantum yield in both highly polar MeOH and lowly polar THF. This indicates that fluorescent compound 5 has a very low responsiveness to environment intrinsic to boron dipyrromethene. It is thought that fluorescent compound 5 emits a similar fluorescence in aqueous solvents having a higher polarity, so that it has the properties indispensable to the application of the compound to biological measurements.

From the data described above, it was proved that fluorescent compound 5 has a maximum absorption in the near infrared wavelength region, and emits an intense and sharp fluorescence even in this wavelength region. Fluorescent compound 5 has optical properties which are one of the best properties among those of the known near infrared fluorescent dyes.

Comparative Example 1

The optical properties of Cy5 (trade name, 1-[3-(4-monomethoxytrityloxy)propyl]-1'-[3-[(2-cyanoethyl)-(N,N-diisopropyl)phosphoramidityl]propyl]-3,3,3',3'-tetramethylindodicarbocyanine chloride) which is a widely used commercially available fluorescent dye were examined in the same manner as in Example 6. The results are shown in Table 2 below. In Table 2, the optical properties of fluorescent compound 5 according to the present invention synthesized in Example 5 are also shown for comparison.

TABLE 2

| Fluorescent Compound | Solvent | $\lambda_{abs}$ [nm] | $\lambda_{flu}$ [nm] | $\epsilon$ [$M^{-1}cm^{-1}$] | $\Phi$ | fwhm [nm] |
|---|---|---|---|---|---|---|
| 5 | MeOH | 664 | 679 | 200,000 | 0.63 | 29 |
| Cy5 | MeOH | 648 | 670 | 250,000 | 0.27[a] | 29 |

[a]the value in PBS obtained from Amersham Biosciences

As shown in Table 2, when compared with the commercially available infrared fluorescent dye Cy5 (trade name) having similar maximum absorption and fluorescence wavelengths, fluorescent compound 5 of the present invention has about the same molar extinction coefficient, and much higher fluorescence quantum yield. Thus, it was shown that fluorescent compound 5 has a possibility to be widely used for more sensitive biological measurements replacing the known near infrared fluorescent dyes.

Comparative Examples 2 to 4

The compound (Comparative Compound 1) described in Patent Literature 1, the compound (Comparative Compound 2) described in Patent Literature 2, and the compound (Comparative Compound 3) represented by the above-described Formula [I] wherein $R^1$ and $R^2$, and $R^6$ and $R^7$, respectively, together form aromatic rings but which do not contain a hetero atom therein, were synthesized, and the optical properties thereof were examined as in Example 6. The structures of Comparative Compounds 1 to 3 are shown below.

Comparative Compound 1

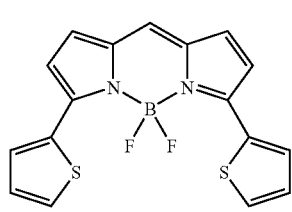

Comparative Compound 2

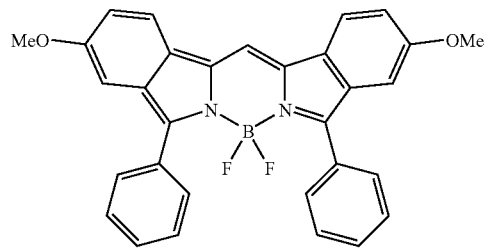

Comparative Compound 3

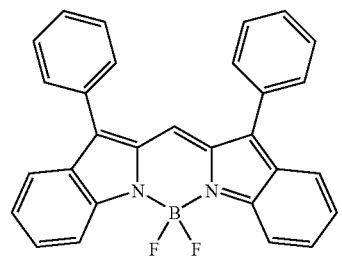

The results are shown in Table 3 below. In Table 3, the optical properties of fluorescent compound 5 according to the present invention synthesized in Example 5 are also shown for comparison.

TABLE 3

| Example | Solvent | $\lambda_{abs}$ [nm] | $\lambda_{flu}$ [nm] | $\epsilon$ [$M^{-1}cm^{-1}$] | $\Phi$ |
|---|---|---|---|---|---|
| Example 5 | CHCl$_3$ | 673 | 685 | 190,000 | 0.68 |
| Example 5 | MeOH | 664 | 679 | 200,000 | 0.63 |
| Comparative Example 2 | CHCl$_3$ | 624 | 637 | 75,500 | 0.50[a] |
| Comparative Example 3 | MeOH | 663 | 690 | 95,700 | 0.57[b] |
| Comparative Example 4 | CHCl$_3$ | 587 | n.d.[c] | 53,000 | n.d.[c] |

[a]Fluorescein ($\Phi$ = 0.92, in 0.1 M NaOH) was used as a reference.
[b]Nile blue ($\Phi$ = 0.25, in MeOH) was used as a reference.
[c]not determined As shown in Table 3, the fluorescent compound of the present invention had a prominently higher molar extinction coefficient and also had a higher fluorescence quantum yield than the compounds of Comparative Examples 2 to 4.

Example 7

Synthesis of Fluorescent Compound 6 of the Present Invention

In accordance with the reaction scheme below, a fluorescent compound 6 of the present invention was synthesized.

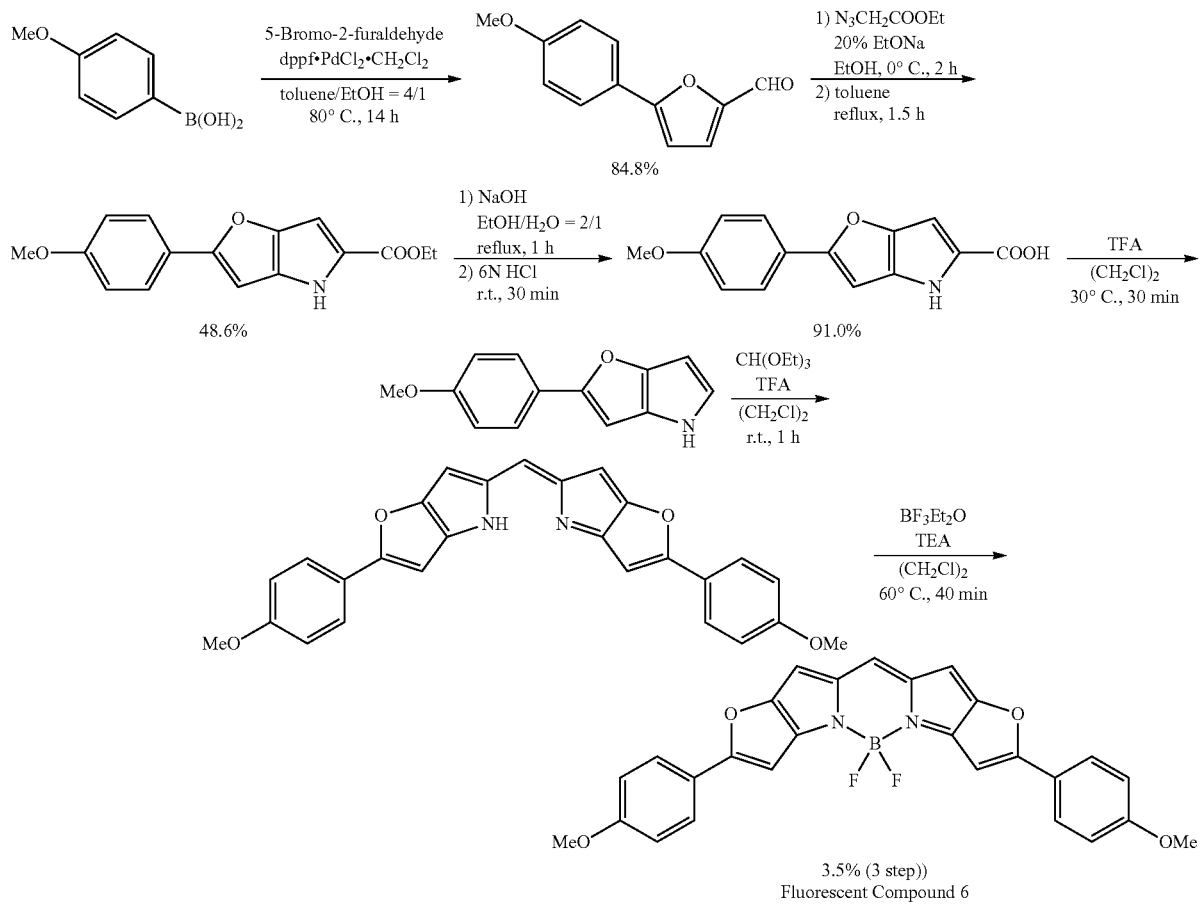

3.5% (3 step))
Fluorescent Compound 6

Synthesis of
5-(4-methoxyphenyl)-furan-2-carboaldehyde (2)

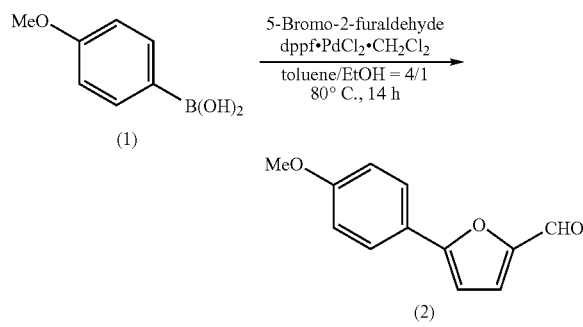

Under Ar gas flow, to a 500 mL three-necked flask, 4-methoxyphenylboronic acid (1) (2.99 g, 19.7 mmol, 1.0 eq) was added and dissolved in toluene (120 ml). [1,1'-bis(diphenylphosphino)-ferrocene]palladium (II) dichloride dichloromethane complex (1:1)(100 mg), ethanol (30 ml), 5-bromo-2-furaldehyde (3.46 g, 19.8 mmol, 1.0 eq) and 2M aqueous sodium carbonate solution (20 ml) were added, and the mixture was stirred for 14 hours at 80° C.

After completion of the reaction, the organic phase was washed with water and saturated brine. After drying the resulting mixture over anhydrous sodium sulfate, the desiccant was removed by filtration and the solvent was concentrated under reduced pressure. The obtained crude product was purified by flash silica gel chromatography (eluent; hexane/ethyl acetate=19/1→4/1) to obtain the desired compound (2) (3.39 g, 84.8%) as pale yellow liquid.

TLC (silica): $R_f$=0.31 (eluent; hexane/ethyl acetate=4/1)

$^1$H-NMR (CDCl$_3$): δ=3.86 (s, 3H), 6.72 (d, 1H, J=3.6 Hz), 6.96 (d, 2H, J=9.0 Hz), 7.30 (d, 1H, J=3.9 Hz), 7.77 (d, 2H, J=9.0 Hz), 9.60 (s, 1H)

Synthesis of 2-azide-3-[5-(4-methoxyphenyl)-furan-2-yl]-acrylic acid ethyl ester (3)

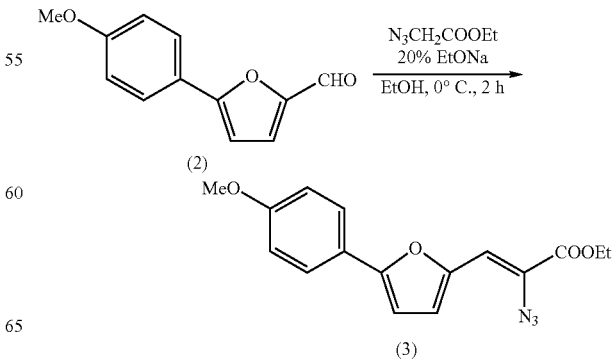

To a 1000 mL three-necked flask, under Ar gas flow, 5-(4-methoxyphenyl)-furan-2-carboaldehyde (2) (3.39 g, 16.8 mmol, 1.0 eq) and ethyl azide acetate (8.65 g, 67.0 mmol, 4.0 eq) were dissolved in ethanol (300 ml), and 20% sodium ethoxide solution (22.8 g, 67.0 mmol, 4.0 eq) in ethanol was slowly added dropwise in an ice bath at 0° C. and stirred for 2 hours.

After completion of the reaction, saturated aqueous ammonium chloride solution was added to change the pH weakly acidic. Water was added thereto and the mixture was subjected to suction filtration, followed by drying of the obtained filtered product to obtain yellow solids (3) (3.31 g). The obtained compound (3) was used as it was in the next reaction without purification.

TLC (silica): $R_f$=0.38 (eluent; hexane/ethyl acetate=9/1)

Synthesis of 2-(4-methoxyphenyl)-4H-furo[3,2-b]pyrrol-5-carboxylic acid ethyl ester (4)

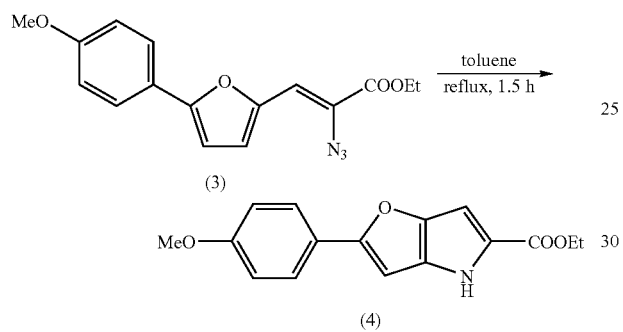

Compound (3) (3.31 g, 10.6 mmol, 1 eq) was added to a 200 mL eggplant type flask, and dissolved in toluene (60 ml), followed by stirring for 1.5 hours under reflux.

After concentration under reduced pressure, the obtained crude product was recrystallized (solution: hexane, ethyl acetate), and the obtained product was subjected to suction filtration, followed by drying the obtained filtered product under vacuum to obtain the desired compound (4)(2.32 g, 48.6% (2 steps)) as brown crystals.

TLC (silica): $R_f$=0.32 (eluent; chloroform)

$^1$H-NMR (CDCl$_3$): δ=1.38 (t, 3H), 3.85 (s, 3H), 4.35 (q, 2H, J=7.1 Hz), 6.58 (s, 1H), 6.80 (s, 1H), 6.94 (d, 2H, J=9.0 Hz), 7.67 (d, 2H, J=9.0 Hz), 8.72 (s, 1H)

Synthesis of 2-(4-methoxyphenyl)-4H-furo[3,2-b]pyrrol-5-carboxylic acid (5)

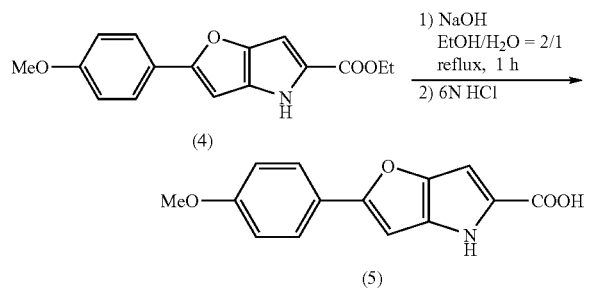

To a 300 mL flask, 2-(4-methoxyphenyl)-4H-furo[3,2-b]pyrrol-5-carboxylic acid ethyl ester (4) (1.90 g, 6.66 mmol, 1 eq) was added and it was dissolved in ethanol (60 ml). A solution (30 ml) of sodium hydroxide (3.90 g, 97.5 mmol, 14.6 eq) in ethanol was added, and the mixture was stirred for 1 hour under reflux.

After allowing the mixture to cool, 6N aqueous HCl solution was added to change the pH acid. Water was added thereto and it was aspiration-filtered. The obtained precipitates were dried under vacuum to obtain the desired compound (5) (1.56 g, 91.0%) as grayish pale green solids.

TLC (silica): $R_f$=0.40 (eluent; ethyl acetate)

$^1$H-NMR (CDCl$_3$): δ=3.86 (s, 3H), 6.60 (s, 1H), 6.83 (s, 1H), 6.95 (d, 2H, J=9.0 Hz), 7.28 (s, 1H), 7.68 (d, 2H, J=9.0 Hz)

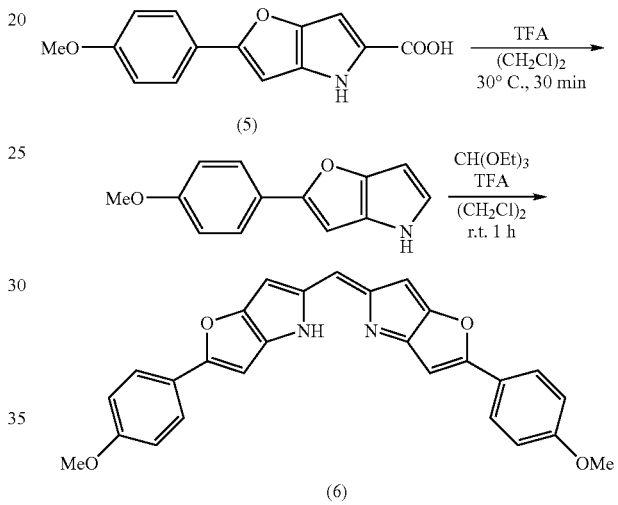

To a 30 mL two-necked flask, 2-(4-methoxyphenyl)-4H-furo[3,2-b]pyrrol-5-carboxylic acid (5) (101 mg, 0.391 mmol, 2 eq), TFA (1 ml) and 1,2-dichloroethane (2 ml) were added and the mixture was stirred under Ar gas flow at 30° C. for 30 minutes. Then 1,2-dichloroethane (6 ml) was added, and after bubbling with nitrogen, triethyl ortho formate (49.8 mg, 0.336 mmol, 1.7 eq) was added, followed by stirring at room temperature for 1 hour.

After completion of the reaction, saturated aqueous sodium hydrogen carbonate solution was added, and the organic phase was washed. The organic phase was washed with saturated brine, and dried over anhydrous sodium sulfate. The obtained crude product was roughly purified by alumina chromatography (eluent: chloroform) to obtain black solids (6) (46.4 mg). The compound (6) was used in the next reaction as it was without purification.

TLC (alumina): $R_f$=0.82 (eluent: chloroform/ethyl acetate=10/1)

Synthesis of Fluorescent Compound 6

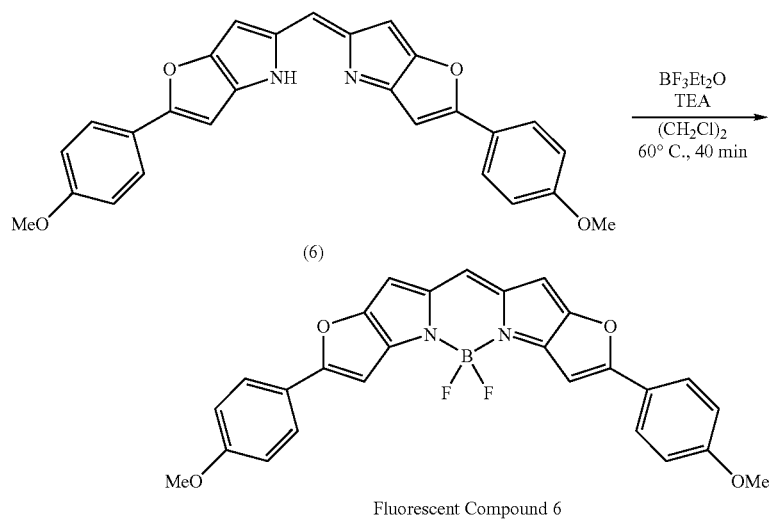

(6)

Fluorescent Compound 6

To a 100 mL flask containing compound (6) (19.9 mg), 1,2-dichloroethane (15 mL), trifluoroboron diethyl ether complex (0.1 mL) and TEA (0.8 mL) were added, and the mixture was stirred at 60° C. for 40 minutes.

After completion of the reaction, ethyl acetate and saturated aqueous sodium hydrogen carbonate solution were added, and the organic phase was extracted and washed. The organic phase was washed with saturated brine and dried over anhydrous sodium sulfate, followed by rough purification of the obtained crude product by silica gel chromatography (eluent: chloroform) to obtain green solids. This product was washed with methanol and acetone, and the obtained solids were dried under vacuum to obtain the fluorescent compound 6 (3.5 mg, 8.5% 3 steps) as green crystals.

TLC (silica): $R_f$=0.24 (eluent: chloroform)

Example 8

Synthesis of Fluorescent Compound 7 of the Present Invention

In accordance with the reaction scheme below, a fluorescent compound 7 of the present invention was synthesized.

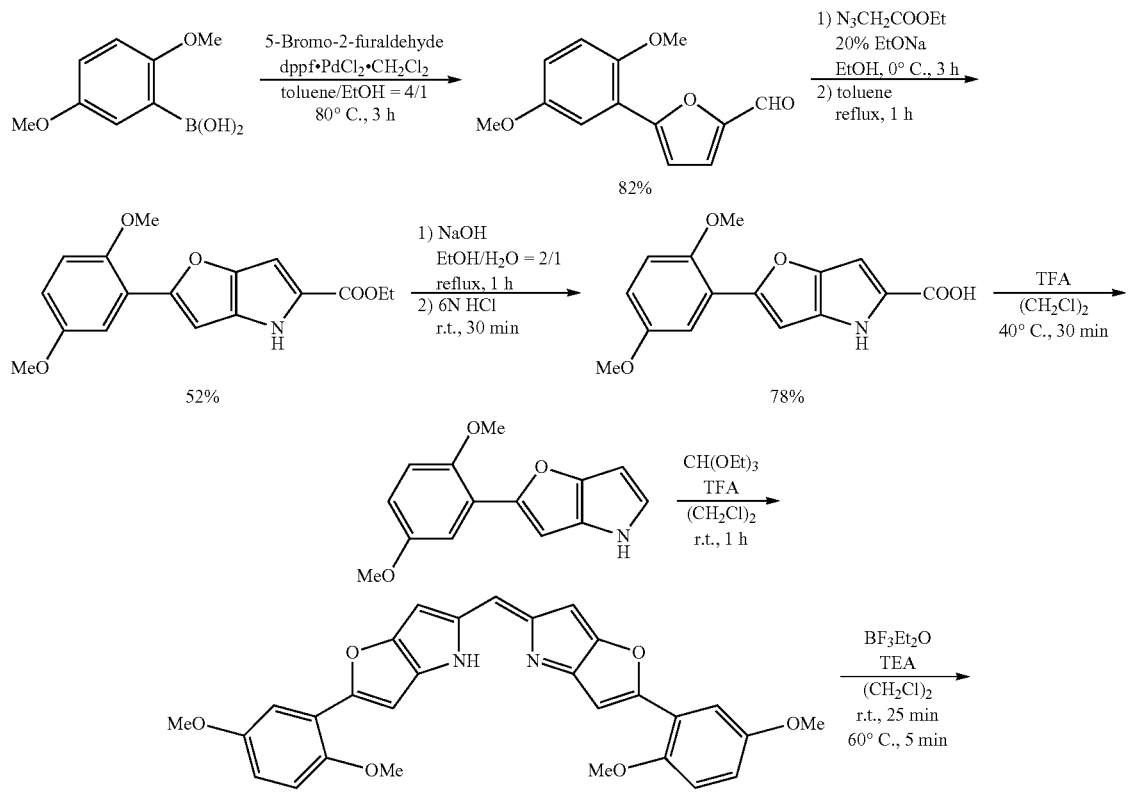

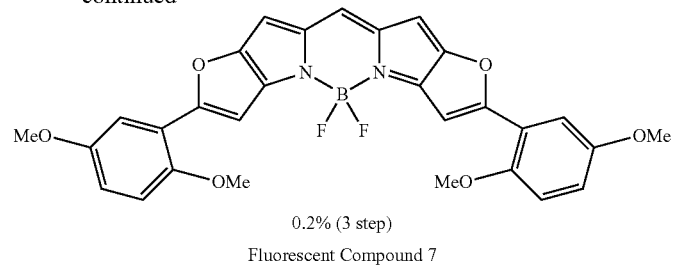

0.2% (3 step)

Fluorescent Compound 7

Synthesis of 5-(2,5-dimethoxyphenyl)-furan-2-carbodialdehyde (9)

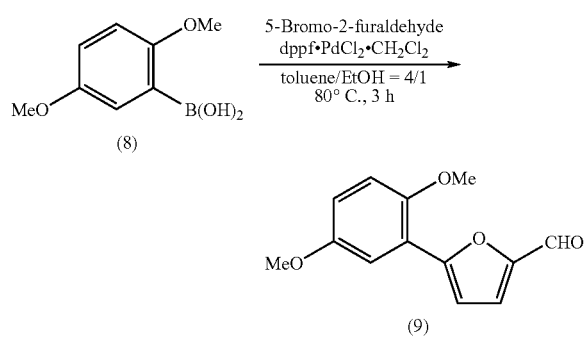

Under Ar gas flow, to a 500 mL three-necked flask, 2,5-dimethoxyphenylboronic acid (8) (3.64 g, 20.0 mmol, 1.0 eq) was added and dissolved in toluene (120 mL). To the mixture, [1,1'-bis(diphenylphosphino)-ferrocene]palladium (II) dichloride dichloromethane complex (1:1) (110 mg), ethanol (30 ml), 5-bromo-2-furoaldehyde (3.50 g, 20.0 mmol, 1.0 eq) and 2M aqueous sodium carbonate solution (20 ml) were added, and the resulting mixture was stirred at 80° C. for 3 hours.

After completion of the reaction, the organic phase was washed with water and saturated brine, and dried over anhydrous sodium sulfate, followed by separation of the desiccant by filtration and concentration of the solvent under reduced pressure. The obtained crude product was purified by silica gel chromatography (eluent: toluene/ethyl acetate=20/1) to obtain the desired compound (9) (3.82 g, 82.2%) as pale yellow liquid.

TLC (silica): $R_f$=0.23 (eluent; toluene/ethyl acetate=20/1)

$^1$H-NMR (CDCl$_3$): δ=3.85 (s, 3H), 3.92 (s, 3H), 6.93 (d, 2H, J=1.7 Hz), 7.17 (d, 1H, J=3.7 Hz), 7.33 (d, 1H, J=3.7 Hz), 7.56 (t, 1H, J=1.7 Hz), 9.65 (s, 1H)

Synthesis of 2-azide-3-[5-(2,5-dimethoxyphenyl)-furan-2-yl]-acrylic acid ethyl ester (10)

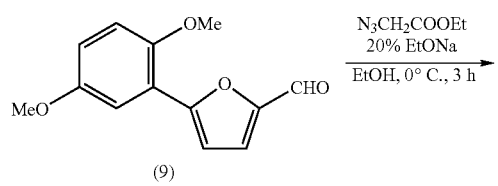

In a 1000 mL three-necked flask, under Ar gas flow, 5-(2,5-dimethoxyphenyl)-furan-2-carboaldehyde (9) (3.82 g, 16.4 mmol, 1.0 eq) and ethyl azide acetate (8.50 g, 65.7 mmol, 4.0 eq) were dissolved in ethanol (300 mL), and then 20% sodium ethoxide solution in ethanol (22.8 g, 65.7 mmol, 4.0 eq) was slowly added dropwise in an ice bath at 0° C., followed by stirring for 3 hours.

After completion of the reaction, saturated aqueous ammonium chloride solution was added to make the pH weakly acidic, and water was added. The mixture was subjected to suction filtration, and the obtained filtered materials were dried to obtain yellow solids (10) (3.30 g) which was used in the next reaction as it was without purification.

TLC (silica): $R_f$=0.61 (eluent: hexane/ethyl acetate=4/1)

Synthesis of Ethyl 2-(2,5-dimethoxyphenyl)-4H-furo[3,2-b]pyrrol-5-carboxylate (11)

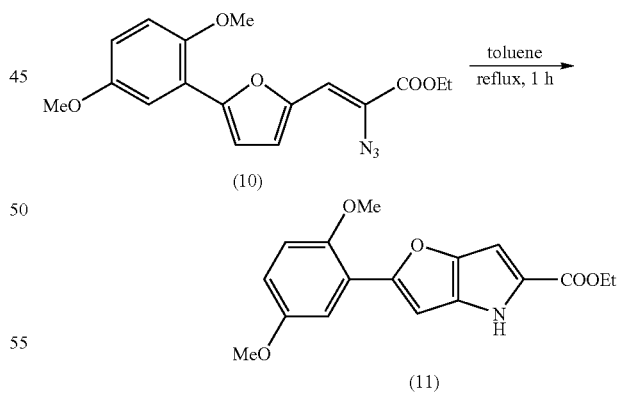

Compound (10) (3.30 g, 9.61 mmol, 1 eq) was placed in a 200 mL eggplant type flask and dissolved in toluene (60 mL), followed by refluxing with stirring for 1 hour.

After concentration of the mixture under reduced pressure, the obtained crude product was recrystallized (solution: hexane, ethyl acetate) and the resultant was subjected to suction filtration, followed by drying the obtained filtered product to obtain the desired compound (11) (2.70 g, 52.1%, 2 steps) as brown crystals.

TLC (silica): R$_f$=0.26 (eluent: chloroform)
$^1$H-NMR (CDCl$_3$): δ=1.39 (t, 3H, J=7.2 Hz), 3.86 (s, 3H), 3.92 (s, 3H), 4.36 (quant., 2H J=7.2 Hz), 6.80-6.84 (m, 2H), 6.90 (d, 1H, J=9.0 Hz), 7.09 (s, 1H), 7.52 (d, 1H, J=3.3 Hz), 8.71 (s, 1H)

Synthesis of 2-(2,5-dimethoxyphenyl)-4H-furo[3,2-b]pyrrol-5-carboxylic acid (12)

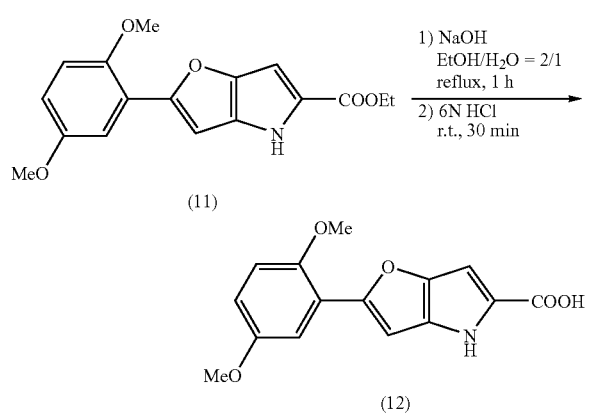

To a 500 mL flask, ethyl 2-(2,5-dimethoxyphenyl)-4H-furo[3,2-b]pyrrol-5-carboxylate (11) (2.67 g, 8.47 mmol, 1 eq) was added and dissolved in ethanol (100 mL). Aqueous sodium hydroxide (5.08 g, 127 mmol, 15 eq) solution (50 mL) was added thereto, and the mixture was refluxed for 1 hour with stirring.

After allowing the mixture to cool, 6N aqueous HCl solution was added to change the solution acidic, and the resulting mixture was stirred for 30 minutes. Water was added thereto and the resulting mixture was subjected to suction filtration, followed by drying the obtained filtered product under vacuum to obtain the desired compound (12) (1.90 g, 78.1%) as grayish green solids.

TLC (silica): R$_f$=0.37 (eluent: ethyl acetate)
$^1$H-NMR (CDCl$_3$): δ=3.86 (s, 3H), 3.92 (s, 3H), 6.84 (dd, 1H, J$_1$=8.8 Hz, J$_2$=2.9 Hz), 6.93-6.89 (m, 2H), 7.11 (s, 1H), 7.52 (d, 1H, J$_2$=2.9 Hz), 8.88 (s, 1H)

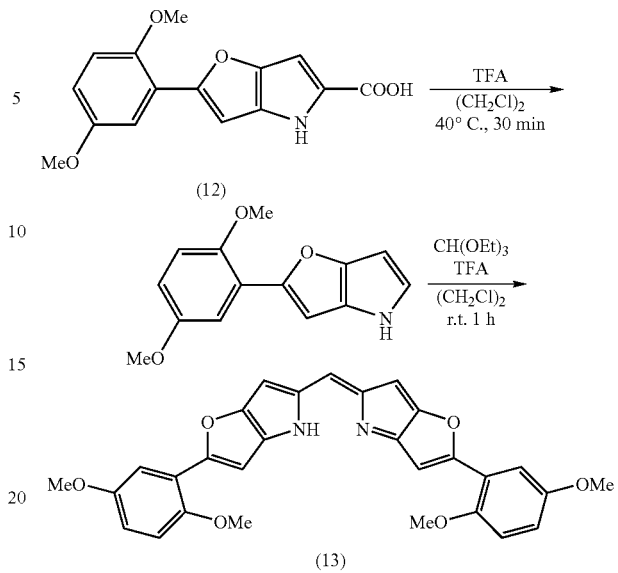

To a 30 mL two-necked flask, 2-(2,5-dimethoxyphenyl)-4H-furo[3,2-b]pyrrol-5-carboxylic acid (12) (97.0 mg, 0.338 mmol, 2 eq), TFA (1 ml) and 1,2-dichloroethane (2 ml) were added, and the mixture was stirred under Ar gas flow at 40° C. for 35 minutes. Then triethyl orthoformate (65.1 mg, 0.439 mmol, 2.6 eq) was added, and the mixture was stirred at room temperature for 40 minutes.

After completion of the reaction, saturated aqueous sodium hydrogen carbonate solution was added, and the organic phase was washed. The organic phase was washed with saturated brine and dried over anhydrous sodium sulfate, followed by rough purification of the obtained crude product by alumina chromatography (eluent: hexane/ethyl acetate=1/1) to obtain violet solids (13) (20.0 mg). Compound (13) was used in the next reaction as it was without purification.

TLC (alumina): R$_f$=0.90 (eluent: chloroform/ethyl acetate=10/1)

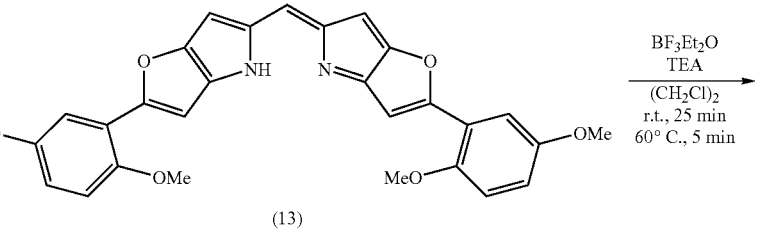

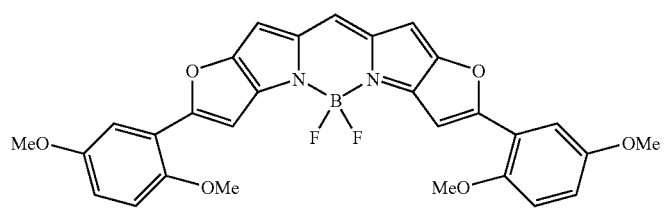

Fluorescent Compound 7

To a 50 mL flask containing compound (13) (20.0 mg), 1,2-dichloroethane (15 mL), trifluoroboron diethyl ether complex (about 0.1 mL) and TEA (about 0.8 mL) were added, and the mixture was stirred at room temperature for 25 minutes and then at 60° C. for 5 minutes.

After completion of the reaction, ethyl acetate and saturated aqueous sodium hydrogen carbonate solution were added, and the organic phase was extracted and washed. The organic phase was washed with saturated brine and dried over anhydrous sodium sulfate, followed by purification by silica gel chromatography (eluent: chloroform), gel permeation chromatography (eluent: special grade chloroform) and preparative thin layer chromatography (eluent: chloroform) to obtain fluorescent compound 7 (0.9 mg, 0.49% (3 steps)) as green crystals.

TLC (silica): $R_f$=0.85 (eluent: chloroform/ethyl acetate=10/1)

$^1$H-NMR (CDCl$_3$): δ=3.86 (s, 6H), 3.97 (s, 6H), 6.47 (s, 2H), 6.95 (d, 4H, J=1.8 Hz), 7.08 (s, 1H), 7.33 (s, 2H), 7.51 (t, 2H, J=1.8 Hz)

Example 9

Synthesis of Fluorescent Compound 8 of the Present Invention

In accordance with the reaction scheme below, a fluorescent compound 8 of the present invention was synthesized.

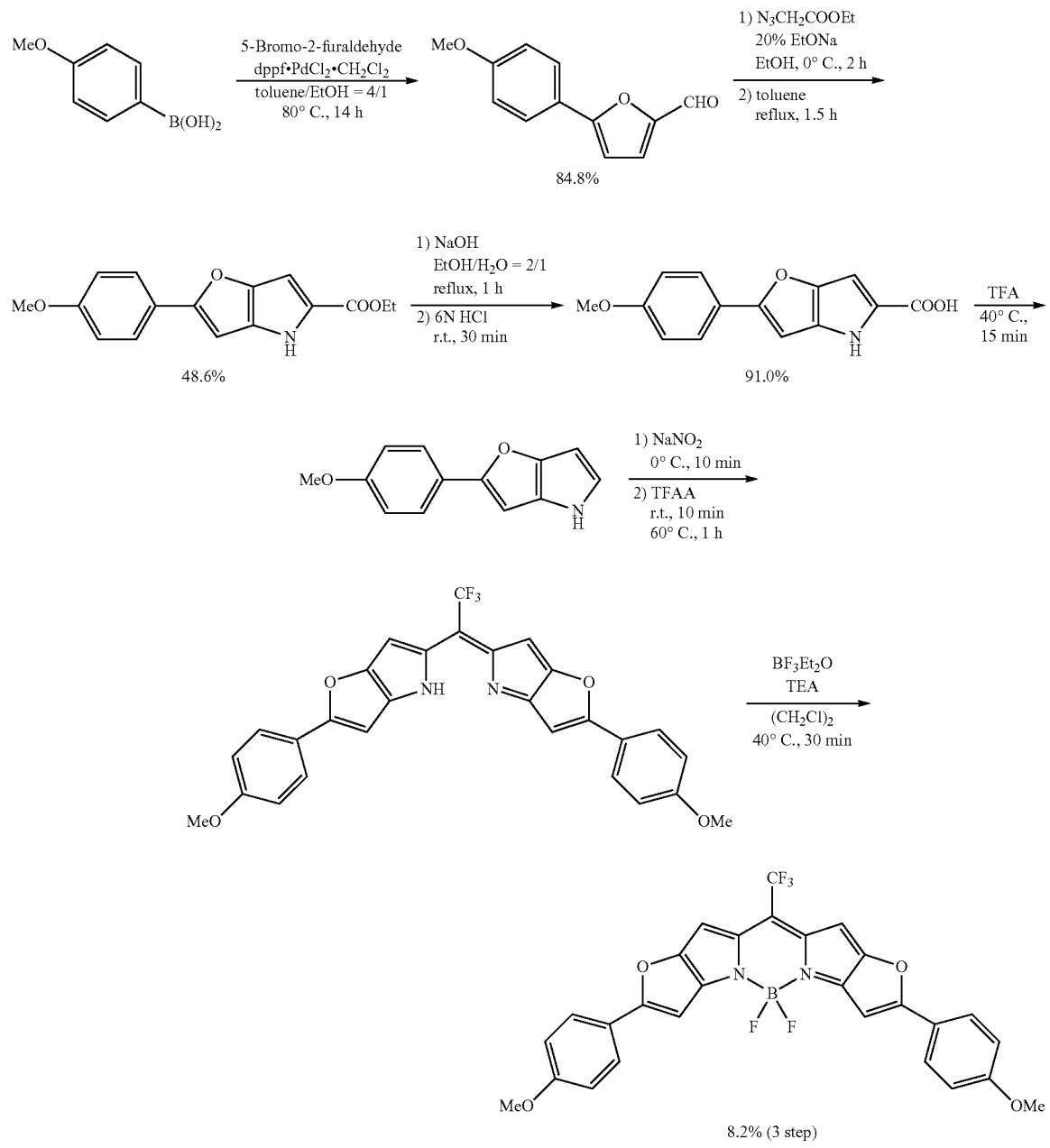

Fluorescent Compound 8

To a 30 mL three-necked flask, 2-(4-methoxyphenyl)-4H-furo[3,2-b]pyrrol-5-carboxylic acid (5) (98.5 mg, 0.38 mmol, 2 eq) and TFA (5 ml) were added, and the mixture was stirred under Ar gas flow at 50° C. for 15 minutes. The mixture was allowed to cool and then cooled in an ice bath at 0° C. Then sodium nitrite (14.2 mg, 0.206 mmol, 1.1 eq) was added and the resulting mixture was stirred at 0° C. for 10 minutes. Then TFAA (2 mL) was added, and the mixture was stirred at room temperature for 10 minutes and then at 60° C. for 1 hour.

After completion of the reaction, saturated aqueous sodium hydrogen carbonate solution and ice were added, the solution was neutralized, ethyl acetate was added, and the organic phase was extracted. The organic phase was washed with water and saturated brine, dried over anhydrous sodium sulfate, followed by rough purification of the obtained crude product by alumina chromatography (eluent: chloroform) to obtain blue green solids (15) (11.5 mg). Compound (15) was used in the next reaction as it was without purification.

TLC (alumina): $R_f$=0.63 (eluent: chloroform)

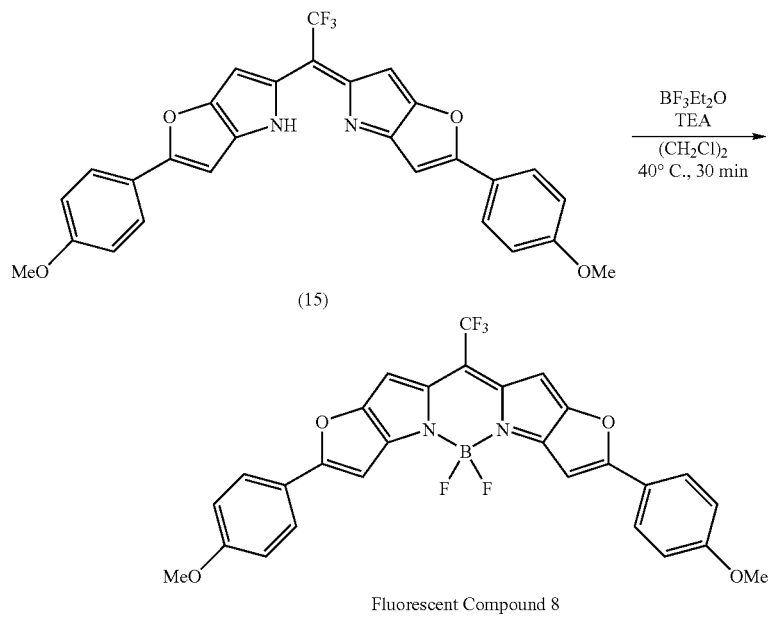

Fluorescent Compound 8

To a 50 mL flask containing compound (15) (11.5 mg), 1,2-dichloroethane (20 mL), trifluoroboron diethyl ether complex (0.1 mL) and TEA (0.08 mL) were added, and the mixture was stirred at 40° C. for 30 minutes.

After completion of the reaction, methylene chloride and saturated aqueous sodium hydrogen carbonate were added, and the organic phase was extracted and washed. The organic layer was washed with saturated brine and dried over anhydrous sodium sulfate, followed by rough purification of the obtained crude product by silica gel chromatography (eluent: chloroform). The resulting product was concentrated under reduced pressure and acetone was added thereto, followed by suction filtration of the resulting product. The obtained filtered product was dried under vacuum to obtain fluorescent compound 8 (9.2 mg, 4.4% (3 steps)) as green crystals.

TLC (silica): $R_f$=0.50 (eluent: chloroform)

$^1$H-NMR (CDCl$_3$): δ=3.90 (s, 6H), 6.73 (quant, 2H, J=2.2 Hz), 6.82 (s, 2H), 7.00 (d, 4H, J=8.8 Hz), 7.80 (d, 4H, J=9.0 Hz)

$^{19}$F-NMR (CDCl$_3$): δ=−54.32 (s, 3F), 149.02 (quant, 2F)

In the above-described Examples and Comparative Examples, the reagents used were of analytical grade or highest grade. All of the $^1$H-NMR spectra were measured using tetramethylsilane as an internal standard at r.t. The apparatuses used were JOEL JNM-GSX300 and JOEL JMM-LA300 FT-NMR.

In the above-described Examples and Comparative Examples, the abbreviations used have the following meanings:

Me: methyl group

Et: ethyl group

DDQ: 2,3-dichloro-5,6-dicyano-p-benzoquinone

TEA: triethylamine

TFA: trifluoroacetic acid

TFAA: trifluoroacetic anhydride

MeOH: methanol r.t.: room temperature min: minute h: hour

Example 10

The optical properties of the fluorescent compounds 6, 7 and 8 of the present invention synthesized in Examples 7 to 9 were measured in the same manner as in Example 6. The results are shown in Table 4 below.

TABLE 4

| Fluorescent Compound | Solvent | $\lambda_{abs}$ [nm] | $\lambda_{fl}$ [nm] | $\epsilon^a$ [M$^{-1}$cm$^{-1}$] | $\Phi^a$ | fwhm (nm) |
|---|---|---|---|---|---|---|
| 6 | CHCl$_3$ | 673 | 683 | 240,000 | 0.69 | 24 |
|   | THF | 665 | 674 | n.d.$^b$ | 0.63 | 24 |
|   | MeOH | 659 | 672 | n.d. | 0.58 | 26 |
| 7 | CHCl$_3$ | 678 | 688 | n.d. | 0.51 | 24 |
|   | MeOH | 662 | 674 | n.d. | 0.54 | 28 |
| 8 | CHCl$_3$ | 722 | 737 | 240,000 | 0.58 | 31 |
|   | Toluene | 724 | 735 | n.d. | 0.53 | 27 |
|   | THF | 721 | 735 | n.d. | 0.42 | 32 |

TABLE 4-continued

| Fluorescent Compound | Solvent | $\lambda_{abs}$ [nm] | $\lambda_{fl}$ [nm] | $\epsilon^a$ [M$^{-1}$cm$^{-1}$] | $\Phi^a$ | fwhm (nm) |
|---|---|---|---|---|---|---|
| | MeCN | 713 | 733 | n.d. | 0.51 | 37 |
| | MeOH | 712 | 732 | n.d. | 0.40 | 35 |

$^a$containing error of 10%
$^b$not determined

The fluorescence quantum yields $\Phi$ of fluorescent compounds 6 and 7 were calculated by using 3,3'-diethyl-dithiazylcarbocyanine ($\Phi$=0.33 in MeOH) as a reference; substituting: A=A$_{ref}$=0.079, $\Phi_{ref}$=0.33, n$_{ref}$=1.329 (MeOH), n=1.445 (CHCl$_3$), 1.407 (THF: tetrahydrofuran), 1.329 (MeOH); and substituting the integrated value of the area of fluorescence intensity detected by excitation with a wavelength of 650 nm for F. The fluorescence quantum yield $\Phi$ is calculated according to the following equation:

$$\Phi=\Phi_{ref}\times(A_{ref}\times F\times n^2)/(A\times F_{ref}\times n_{ref}^2)$$

(wherein A represents absorbance, F represents integrated value of wave number of fluorescent spectrum; n represents the refractive index of the solvent; and "ref" represents the reference dye.

The fluorescence quantum yield $\Phi$ of fluorescent compounds 8 was determined by preparing solutions thereof having different concentrations; preparing a graph taking the integrated value F (excitation light: 690 nm) of the area of fluorescence intensity along the ordinate and taking the absorbance A along the abscissa; calculating the slope Grad (=F/A) thereof; and substituting it and the refractive indices n=1.496 (toluene), 1.445 (CHCl$_3$), 1.407 (THF), 1.344 (MeCN) and 1.329 (MeOH) of the respective solvents for the equation below, respectively. Here, reference compound 1 (described below) ($\Phi_{ref}$=0.36, in CHCl$_3$) was used as a reference.

$$\Phi=\Phi_{ref}\times(\text{Grad}\times n^2)/(\text{Grad}_{ref}\times n_{ref}^2)$$

(wherein Grad represents the slope of the graph taking the integrated value F of the area of fluorescence intensity along the ordinate and taking the absorbance along the abscissa; n represents the refractive index of the solvent; and ref represents the reference dye).

The maximum absorption wavelengths of fluorescent compounds 6 and 7 were 683 nm and 688 nm, respectively, so that the maximum absorption wavelengths were shifted to longer wavelengths by about 170 nm when compared with boron dipyrromethene (R$_1$=R$_3$=R$_5$=R$_7$=Me) and by about 90 nm when compared with fluorescent compound 2. By this, it was proved that the wavelength is shifted to longer wavelength by introducing electron donating groups at specific sites. Further, fluorescent compounds 6 and 7 have a very small full width at half maximum height and so have a sharp fluorescence spectrum. These results indicate that the fluorescence wavelengths were shifted to longer wavelength retaining the stiffness of the skeleton comparable to that of the boron dipyrromethene skeleton. Still further, by comparison between fluorescent compounds 6 and 7, it was proved that the higher the electron donating property of the introduced groups, the larger the amount of the shift to longer wavelength.

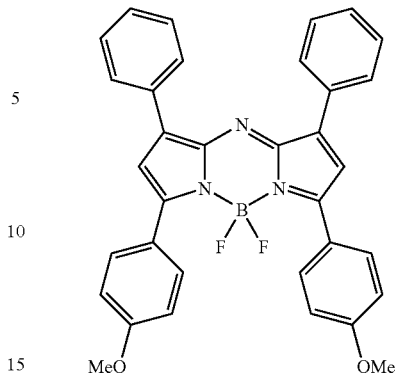

Reference Compound 1

The maximum fluorescence wavelength of fluorescent compound 8 was 737 nm in chloroform, so that the maximum wavelength was shifted longer by about 54 nm than fluorescent compound 6. This shows that further shift to longer wavelength can be attained by introducing electron donating groups to the specific sites. Further, fluorescent compound 8 has a very small full width at half maximum height as small as about 31 nm and so has a sharp fluorescence spectrum. These results indicate that the fluorescence wavelength was shifted to longer wavelength retaining the stiffness of the skeleton comparable to that of the boron dipyrromethene skeleton.

Example 11

An experiment testing the light fastness of fluorescent compound 8 and Cy7 (trade name, 1-[3-(4-monomethoxytrityloxy)propyl]-1'-[3-[(2-cyanoethyl)-(N,N-diisopropyl)phosphoramidityl]propyl]-3,3,3',3'-tetramethylindotricarbocyanine chloride) was carried out.

Fluorescent compound 8 and Cy7 (trade name) were respectively dissolved in acetonitrile to a concentration attaining an absorbance of 0.1. The solutions were left to stand under the same conditions (more specifically, under the light of daily life without light shading, and the absorbance was measured every day (or every other day). The change with time of the measured absorbance was graphed taking the relative absorbance (taking the absorbance before leaving to stand as 100%) along the ordinate and taking the days along the abscissa.

The results are shown in FIG. 1. Fluorescent compound 8 retained the absorbance of 95% or more even after 1 week. On the other hand, the absorbance of Cy7 (trade name) was decreased to 10% or less within the same period. These results show that while the light fastness of Cy7 (trade name) is very poor, fluorescent compound 8 has a very high light fastness. Thus, it is thought that the compound can be applied to analysis reagent used for a long time or used as a novel dye material or optical material having a high durability, which could not be attained by the conventional dyes.

As mentioned in paragraph 0010, cyanine dyes represented by Cy7 has a long olefin (polymethine) chain which is chemically flexible, and it is thought that this part was subjected to photoisomerization or the like, which resulted in the decrease in the durability. This phenomenon may occur generally not only in Cy7 but also in other dyes having olefin (polymethine) structure, and it is thought that the longer the olefin (polymethine) chain, the more the decrease in durability. It should be noted that this phenomenon has been reported in many references including Non-patent Literature 3.

On the other hand, it is thought that the light fastness of fluorescent compound 8 was drastically improved because the compound has a chemically stiff molecular structure. Therefore, fluorescent compound 8 has an advantage in the light fastness over the dyes having a flexible olefin structure, especially, over cyanine dyes represented by Cy7. It should be noted, however, occurrence of this phenomenon is not limited to fluorescent compound 8, but is common to the fluorescent compounds according to the present invention.

The invention claimed is:

1. A fluorescent compound having the structure represented by the following Formula [I]:

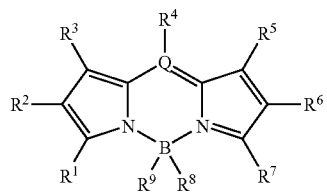

[I]

wherein
  $R^1$ and $R^2$ together form a 5-membered or 6-membered hetero ring containing at least one hetero atom selected from the group consisting of sulfur, oxygen, nitrogen and phosphorus, or when they do not form said hetero ring, $R^1$ and $R^2$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;
  $R^6$ and $R^7$ together form a 5-membered or 6-membered hetero ring containing at least one hetero atom selected from the group consisting of sulfur, oxygen, nitrogen and phosphorus, or when they do not form said hetero ring, $R^6$ and $R^7$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;
  at least one of (1) $R^1$ and $R^2$, and $R^6$ and $R^7$ form said hetero ring;

Q represents a carbon atom or nitrogen atom;
  $R^3$, $R^4$ and $R^5$ independently represent a hydrogen atom or a group which does not inhibit the fluorescence of said compound (provided that when Q is a nitrogen atom, $R^4$ does not exist) selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups; and
  $R^8$ and $R^9$ independently represent a halogen atom, alkyl group, alkenyl group, alkynyl group, alkoxy group, aryl group, or heteroaryl group.

2. The compound according to claim 1, wherein said hetero ring(s) formed by said $R^1$ and $R^2$, and/or said $R^6$ and $R^7$ independently has(have) a structure represented by the following:

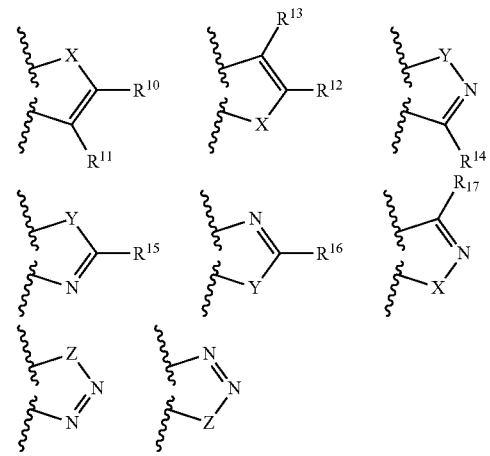

wherein in these formulae, X, Y and Z independently represent sulfur, oxygen, nitrogen or phosphorus atom; $R^{10}$ to $R^{17}$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups.

3. The compound according to claim 2, wherein said hetero ring(s) has(have) a structure represented by the following:

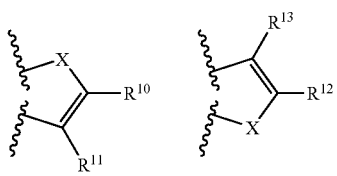

wherein in these formulae, X, Y and Z independently represent sulfur, oxygen, nitrogen or phosphorus atom; $R^{10}$ to $R^{13}$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups.

4. The compound according to claim 2 or 3, wherein said $R^{10}$ to $R^{17}$ independently represent a hydrogen atom or an electron donating group.

5. The compound according to claim 4, wherein said electron donating group is an alkyl group, phenyl group, p-alkoxyphenyl group, p-dialkylaminophenyl group, 2-thienyl group, 2-furyl group or dialkoxyphenyl group.

6. The compound according to claim 5, wherein said electron donating group is a $C_1$-$C_{10}$ alkyl group, alkoxyphenol group whose alkyl moiety has 1 to 10 carbon atoms, or dialkoxyphenyl group whose respective alkyl moieties have 1 to 10 carbon atoms.

7. The compound according to claim 1, wherein in said Formula [I], $R^8$ and $R^9$ are each independently a halogen atom.

8. The compound according to claim 7, wherein said Formula [I], $R^8$ and $R^9$ are each a fluorine atom.

9. A method for measuring a labeled substance, said method comprising:
subjecting a substance labeled with a fluorescent compound having the structure represented by the following Formula [I]:

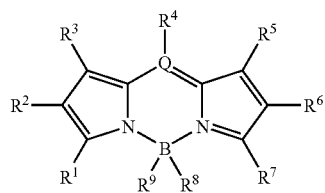

wherein
$R^1$ and $R^2$ together form a 5-membered or 6-membered hetero ring containing at least one hetero atom selected from the group consisting of sulfur, oxygen, nitrogen and phosphorus, or when the they do not form said hetero ring, $R^1$ and $R^2$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;

$R^6$ and $R^7$ together form a 5-membered or 6-membered hetero ring containing at least one hetero atom selected from the group consisting of sulfur, oxygen, nitrogen and phosphorus, or when they do not form said hetero ring, $R^6$ and $R^7$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;

at least one of (1) $R^1$ and $R^2$, and $R^6$ and $R^7$ form said hetero ring;

Q represents a carbon atom or nitrogen atom;

$R^3$, $R^4$ and $R^5$ independently represent a hydrogen atom or a group which does not inhibit the fluorescence of said compound (provided that when Q is a nitrogen atom, $R^4$ does not exist) selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups; and $R^8$ and $R^9$ independently represent a halogen atom, alkyl group, alkenyl group, alkynyl group, alkoxy group, aryl group, or heteroaryl group to a reaction; and after said reaction, measuring said substance with making said fluorescent compound emit light.

10. A biological substance labeled with compound of the formula

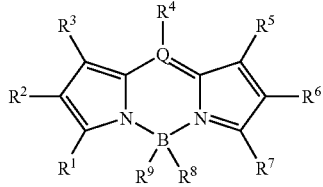

wherein
- $R^1$ and $R^2$ together form a 5-membered or 6-membered hetero ring containing at least one hetero atom selected from the group consisting of sulfur, oxygen, nitrogen and phosphorus, or when the they do not form said hetero ring, $R^1$ and $R^2$ independently represent a hydrogen atom or a group which does not inhibit the fluorescence of said compound selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;
- $R^6$ and $R^7$ together form a 5-membered or 6-membered hetero ring containing at least one hetero atom selected from the group consisting of sulfur, oxygen, nitrogen and phosphorus, or when they do not form said hetero ring, $R^6$ and $R^7$ independently represent a hydrogen atom or a group which does not inhibit the fluorescence of said compound selected from the following:
  halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups;
- at least one of (1) $R^1$ and $R^2$, and $R^6$ and $R^7$ form said hetero ring;
- Q represents a carbon atom or nitrogen atom;
- $R^3$, $R^4$ and $R^5$ independently represent a hydrogen atom or a group which does not inhibit the fluorescence of said compound (provided that when Q is a nitrogen atom, $R^4$ does not exist) selected from the following: halogen atom, nitro group, cyano group, hydroxyl group, amino group, thiol group, carboxyl group, aldehyde group, sulfonic group, isocyanate group, thioisocyanate group, alkyl groups, alkenyl groups, alkynyl groups, alkoxy groups, alkoxycarbonyl groups, acyl groups, halogenoacyl groups, monoalkylamino groups, dialkylamino groups, alkylthio groups, alkylcarbonylamide groups, alkylamide carbonyl groups, monoalkylsilyl groups, dialkylsilyl groups, trialkylsilyl groups, monoalkoxysilyl groups, dialkoxysilyl groups, trialkoxysilyl groups, alkylsulfonyl groups, halogenosulfonyl groups, aryl groups and heteroaryl groups; and
- $R^8$ and $R^9$ independently represent a halogen atom, alkyl group, alkenyl group, alkynyl group, alkoxy group, aryl group, or heteroaryl group.

11. A labeled biological substance according to claim 10, wherein the biological substance is a protein, polypeptide, antibody or sugar.

12. A labeled biological substance according to claim 10, wherein the biological substance is chemical bound to a compound of Formula [I].

13. The compound according to claim 1, wherein said $R^4$, $R^{10}$, $R^{12}$, $R^{15}$ or $R^{16}$ is a group that recognizes an ion or molecule.

14. The compound according to claim 13, wherein said group that recognizes an ion or molecule is a benzocrown, azacrown, or N-arylazacrown.

* * * * *